(12) United States Patent
Kamiya et al.

(10) Patent No.: US 10,502,704 B2
(45) Date of Patent: Dec. 10, 2019

(54) GAS SENSOR PROVIDED WITH FLANGE PORTION OF COVER THEREOF

(71) Applicant: DENSO CORPORATION, Kariya, Aichi-pref. (JP)

(72) Inventors: Yasutaka Kamiya, Kariya (JP); Yoshihide Segawa, Kariya (JP); Hirokazu Yamada, Kariya (JP)

(73) Assignee: DENSO CORPORATION, Kariya (JP)

( * ) Notice: Subject to any disclaimer, the term of this patent is extended or adjusted under 35 U.S.C. 154(b) by 144 days.

(21) Appl. No.: 15/886,063

(22) Filed: Feb. 1, 2018

(65) Prior Publication Data

US 2018/0217090 A1 Aug. 2, 2018

(30) Foreign Application Priority Data

Feb. 2, 2017 (JP) .................................. 2017-017788

(51) Int. Cl.
| | |
|---|---|
| *G01N 27/407* | (2006.01) |
| *G01N 27/403* | (2006.01) |
| *F01N 13/00* | (2010.01) |
| *G01M 15/10* | (2006.01) |
| *G01N 27/406* | (2006.01) |
| *G01N 27/41* | (2006.01) |
| *G01N 33/00* | (2006.01) |

(52) U.S. Cl.
CPC ....... *G01N 27/4078* (2013.01); *F01N 13/008* (2013.01); *G01M 15/104* (2013.01); *G01N 27/4067* (2013.01); *G01N 27/4071* (2013.01); *G01N 27/41* (2013.01); *G01N 33/0037* (2013.01); *F01N 2560/02* (2013.01); *F01N 2560/025* (2013.01); *Y02A 50/245* (2018.01)

(58) Field of Classification Search
CPC .. G01N 27/406; G01N 27/407; G01N 27/416; G01N 27/409; G01N 27/4077; G01N 27/4078

See application file for complete search history.

(56) References Cited

U.S. PATENT DOCUMENTS

| | | | |
|---|---|---|---|
| 4,019,974 A | * | 4/1977 | Weyl .................. G01N 27/4062 204/428 |
| 5,795,454 A | | 8/1998 | Friese et al. |
| 6,214,186 B1 | | 4/2001 | Watanabe et al. |

(Continued)

FOREIGN PATENT DOCUMENTS

| | | |
|---|---|---|
| JP | 11-190715 | 7/1999 |
| JP | 2012-083327 | 4/2012 |

(Continued)

*Primary Examiner* — Susan D Leong
(74) *Attorney, Agent, or Firm* — Nixon & Vanderhye P.C.

(57) ABSTRACT

A gas sensor includes a sensor element having a detecting portion; an insulator supporting the sensor element inserted therethrough; a housing supporting the insulator; an inner cover covering the detecting portion; and an outer cover covering the inner cover. An inner flange portion of the inner cover and the outer flange portion of the outer cover are supported between the insulator and the housing. An end face of the inner flange portion is positioned towards outer side R1 with respect to the radial direction R than the position of an end face of the outer flange portion. A corner portion between the end face and a surface in the outer flange portion protrudes into a surface of the inner flange portion.

6 Claims, 23 Drawing Sheets

(56) References Cited

U.S. PATENT DOCUMENTS

| | | | |
|---|---|---|---|
| 2002/0144538 A1* | 10/2002 | Yamada | G01N 27/4062 |
| | | | 73/31.05 |
| 2006/0065541 A1* | 3/2006 | Nishio | G01N 27/4077 |
| | | | 205/427 |
| 2012/0031171 A1 | 2/2012 | Masuda et al. | |
| 2017/0010235 A1 | 1/2017 | Nakamura | |
| 2017/0089852 A1* | 3/2017 | Watanabe | G01N 27/028 |
| 2017/0315082 A1 | 11/2017 | Kawamoto et al. | |

FOREIGN PATENT DOCUMENTS

| | | |
|---|---|---|
| JP | 2015-108583 | 6/2015 |
| JP | 2015-210147 | 11/2015 |
| JP | 2015-219097 | 12/2015 |
| JP | 2016-011885 | 1/2016 |
| WO | 89/03528 | 4/1989 |

\* cited by examiner

GAS SENSOR PROVIDED WITH FLANGE PORTION OF COVER THEREOF

CROSS-REFERENCE TO RELATED APPLICATION

This application is based on and claims the benefit of priority from earlier Japanese Patent Application No. 2017-17788 filed Feb. 2, 2017, the description of which is incorporated herein by reference.

BACKGROUND

Technical Field

The present disclosure relates to a gas sensor having a structure that covers a detecting portion of a sensor element.

Description of the Related Art

A gas sensor is disposed in a pipe of an exhaust system of an internal combustion engine and detects an exhaust gas flowing through the pipe as detection gas. The gas sensor performs gas detection utilizing a change in an oxygen concentration in the detection gas. The usage of the gas sensor incudes detection of the oxygen concentration in the exhaust gas exhausted from the internal combustion engine, detection of an air fuel ratio (A/F) of the internal combustion engine from the exhaust gas, detection of whether the A/F obtained from the exhaust gas is a fuel rich side or a fuel lean side with respect to the theoretical A/F value, and detection of specific gas such as NOx.

The gas sensor uses a sensor element having a solid electrolyte and a pair of electrodes. The sensor element is provided with a detecting portion where the detection gas is lead to one of electrodes to perform the gas detection. The sensor element is supported by an insulator having insulation properties in a state where the detecting portion is protruded therefrom. The insulator is supported in a housing which is attached to the exhaust pipe or the like. In the housing, a cover is attached covering the detecting portion of the sensor element to prevent the sensor element from being exposed to the water. In the cover, through holes are formed to allow the detection gas to flow into the detecting portion.

Also, the cover is constituted to have double structure including an inside cover and an outside cover, to make the detecting portion of the sensor element less exposed to the water. For example, Japanese patent application laid-open publication number 2015-210147 discloses a gas sensor in which a flange portion of an inner cover is supported between the hosing and the insulator and the inner cover and the outer cover are fixed by a welding portion. Then, the welding portion is formed in a shape expanded towards the outer periphery, whereby heat of the exhaust gas propagated to the welding portion can be radiated to the housing.

Further, Japanese patent application laid-open publication number 2015-210146 discloses a gas sensor in which a flange portion of an inner cover is supported between the housing and the insulator while a convex portion provided in either one of the inner cover or the housing is protruded into the other one. Hence, the positional relationship between the hosing and the inner cover is prevented from being displaced. Also, the patent document (Japanese patent application laid-open publication number 2015-210146) discloses that the flange portion of the inner cover and the flange portion of the outer cover may be supported between the housing and the insulator.

In recent years, the thermal environment has become more severe in the exhaust system to which a gas sensor is mounted. For example, in the case where the gas sensor is mounted in an upper stream side of the supercharger, the thermal shock to the gas sensor becomes large, since the gas sensor is likely to be rapidly heated in addition to the fact that the maximum temperature of the exhaust gas is higher than other part. Also, in the case where gas sensors are mounted to a vehicle adapted for an idling stop or a hybrid vehicle, the engine is frequently stopped, whereby the gas sensors are easily cooled so that the thermal shock becomes more significant.

According to a gas sensor disclosed by the above-mentioned patent document, i.e., Japanese patent application laid-open publication number 2015-210147, when the welding portion between the inner cover and the outer cover is exposed to the exhaust gas, thereby being heated to high temperature, the strength of the welding portion is lowered because of fatigue. Hence, the lowered strength may cause separation of the inner cover and the outer cover. Similarly, in the gas sensor disclosed in the above-mentioned patent document, i.e., Japanese patent application laid-open publication number 2015-210146, the same problem arises when the inner cover and the outer cover are fixed by welding.

According to a structure disclosed by the patent document 2015-210146, in which flange portion of the inner cover and the flange portion of the outer cover are supported between the housing and the insulator, welding portion can be removed. However, it has been found that ingenious design is required for the structure between the flange portion of the inner cover and the outer cover, to secure sufficient air-tightness therebetween. In the case where the exhaust gas enters into the gas sensor from a gap between the flange portion of the inner cover and the flange portion of the outer cover, detection accuracy of the gas sensor to detect the gas may be deteriorated.

SUMMARY

The embodiment provides a gas sensor capable of maintaining high accuracy of the gas detection, in which the inner cover or the outer cover thereof is prevented from separating from the gas sensor during the operation, and high air tightness between the insulator and the housing is maintained.

An aspect of the present disclosure is a gas sensor includes: a sensor element having a detecting portion exposed to detection gas to perform gas detection; an insulator made of a ceramic material, supporting the sensor element in a state where the detecting portion is protruded therefrom, the sensor element being inserted through the insulator; a housing made of metal disposed in an outer periphery of the insulator, supporting the insulator; an inner cover made of metal, covering the detecting portion and having an inner through hole that allows the detection gas to flow therethrough; and an outer cover made of metal, covering the inner cover such that a gas passage through which the detection gas flows is formed between the outer cover and the inner cover and having an outer through hole that allows the detection gas to flow therethrough.

In the gas sensor, an inner flange portion formed over an entire periphery of an end portion of the inner cover and an outer flange portion formed over an entire periphery of an end portion of the outer cover are supported between the insulator and the housing; an end face of the inner flange portion and an end face of the outer flange portion are mutually offset; a corner portion is formed between the end face and a surface in either one of the inner flange portion and the outer flange portion; and the corner portion formed in either one of the inner flange portion and the outer flange portion protrudes into the surface of the other flange portion, or an end portion in either one of the inner flange portion and the outer flange portion is bent to overhang the corner portion in the other flange portion formed between the end face and the surface.

Another aspect of the present disclosure is a gas sensor including: a sensor element having a detecting portion exposed to detection gas to perform gas detection; an insulator made of a ceramic material, supporting the sensor element in a state where the detecting portion is protruded therefrom, the sensor element being inserted through the insulator; a housing made of metal disposed in an outer periphery of the insulator, supporting the insulator; an inner cover made of metal, covering the detecting portion and having an inner through hole that allows the detection gas to flow therethrough; and an outer cover made of metal, covering the inner cover such that a gas passage through which the detection gas flows.

In the gas sensor, an inner flange portion formed over an entire periphery of an end portion of the inner cover and an outer flange portion formed over an entire periphery of an end portion of the outer cover are supported between the insulator and the housing; a protrusion is formed on a surface in either one of the inner flange portion and the outer flange portion; and the protrusion formed in either one of the inner flange portion and the outer flange portion protrudes into the surface of the other flange portion, or an end portion in either one of the inner flange portion and the outer flange portion is bent to overhang the protrusion formed on the surface in the other flange portion.

According to one aspect of the gas sensor, both of the inner flange portion of the inner cover and the outer flange portion of the outer cover are supported between the insulator and the housing. In other words, unlike a case where a flange portion between the insulator and the housing is formed only in the inner cover or the outer cover, the inner cover and the outer cover can reliably be prevented from separating from the gas sensor.

In the case where the flange portion is formed in either one of the inner cover and the outer cover only, the other one of the cover has to be joined to either one of the cover by welding or the like. This joint is required to have enough strength to join the one cover to the other cover so that volume of the joint portion increases.

Therefore, when the conventional gas sensor is heated to high temperature when operating, the strength of the inner cover and the outer cover is significantly lowered at the joint portion thereof, which may cause the inner cover and the outer cover to detach from the gas sensor. On the other hand, according to the above-described gas sensor in which both of the inner flange portion of the inner cover and the outer flange portion of the outer cover are supported between the insulator and the housing, a joint portion having large volume is not necessary. Hence, during the operation, the inner cover and the outer cover can be prevented from separating from the gas sensor.

It is preferable that a joint portion by welding or the like is not formed between the inner cylindrical portion of the inner cover and the outer cylindrical portion of the outer cover. However, a small joint portion having a small volume using a welding or the like can be provided between the inner cover and the outer cover to maintain the positional relationship therebetween. The volume of the joint portion can be determined such that a degree of lowered strength during heating does not exceed a specified range that prevents the inner cover and the outer cover from separating from the gas sensor.

Also, according to the above-described gas sensor, the end face of the inner flange portion and the end face of the outer flange portion are mutually offset to form a state where the corner portion protrudes into the surface, or a state where the end face is bent to overhang the corner portion. Thus, high air tightness between the insulator and the housing can be maintained so that high accuracy of the gas detection can be maintained. Since the end face of the inner flange portion and the end face of the outer flange portion are mutually offset, the state of intrusion or the state of bending can readily be provided without any special contrivance.

Assuming that the air tightness decreases between the insulator and the housing so that the exhaust gas of the internal combustion engine as the detection gas enters inside the gas sensor through a gap between the insulator and the housing, the detection gas may be mixed with the reference gas such as atmospheric air used for performing gas detection by the detecting portion of the sensor element. In this case, since the gas detection utilizes difference between the oxygen concentration in the reference gas and the oxygen concentration of the detection gas, the detection accuracy may be degraded.

The state of the positional offset and the state of intrusion or the state of bending are provided, whereby a gap is unlikely to be formed between the inner flange portion and the outer flange portion during the operation of the gas sensor. Therefore, air tightness between the insulator and the housing can be maintained to be high. These features will be later described in detail in the embodiment section.

Thus, according to the above-described aspect of the gas sensor, during the operation, the inner cover and the outer cover is prevented from separating from the gas sensor and the air tightness between the insulator and the housing is maintained to be high so that detection accuracy of the gas detection can be maintained to be high.

According to another aspect of the gas sensor, a protrusion is provided on a surface of either one of the inner flange portion and the outer flange portion. Then, instead of using a corner portion between the surface and the end face, the protrusion is used to form the state of intrusion or the state of bending. Hence, according to another aspect of the gas sensor, it is not necessary to have a mutual offset between the end face of the inner flange portion and the end face of the outer flange portion. The end face of the inner flange portion and the end face of the outer flange portion may be offset or may be flush with each other.

Similarly, according to other aspect of the gas sensor, during the operation, the inner cover and the outer cover is prevented from separating from the gas sensor and the air tightness between the insulator and the housing is maintained to be high so that detection accuracy of the gas detection can be maintained to be high.

It should be noted that contents of the gas detection of the sensor element includes detection of the oxygen concentration of the exhaust gas exhausted by the internal combustion engine, detection of the air-fuel ratio of the internal combustion engine which is calculated from the exhaust gas, detection of whether the air-fuel ratio calculated from the exhausted gas is in a fuel rich side or fuel lean side with respect to the theoretical air-fuel ratio, and detection of specific gas components such as NOx.

Note that reference signs in parenthesis of respective elements shown in one aspect of the present disclosure represent correspondence with the reference signs in the drawings for embodiments, but the respective elements are not limited to contents of the embodiments of the present disclosure.

DETAILED DESCRIPTION OF PREFERRED EMBODIMENTS

With reference to the drawings, preferred embodiments of gas sensors according to the present disclosure will be described.

(First Embodiment)

Figure 1:
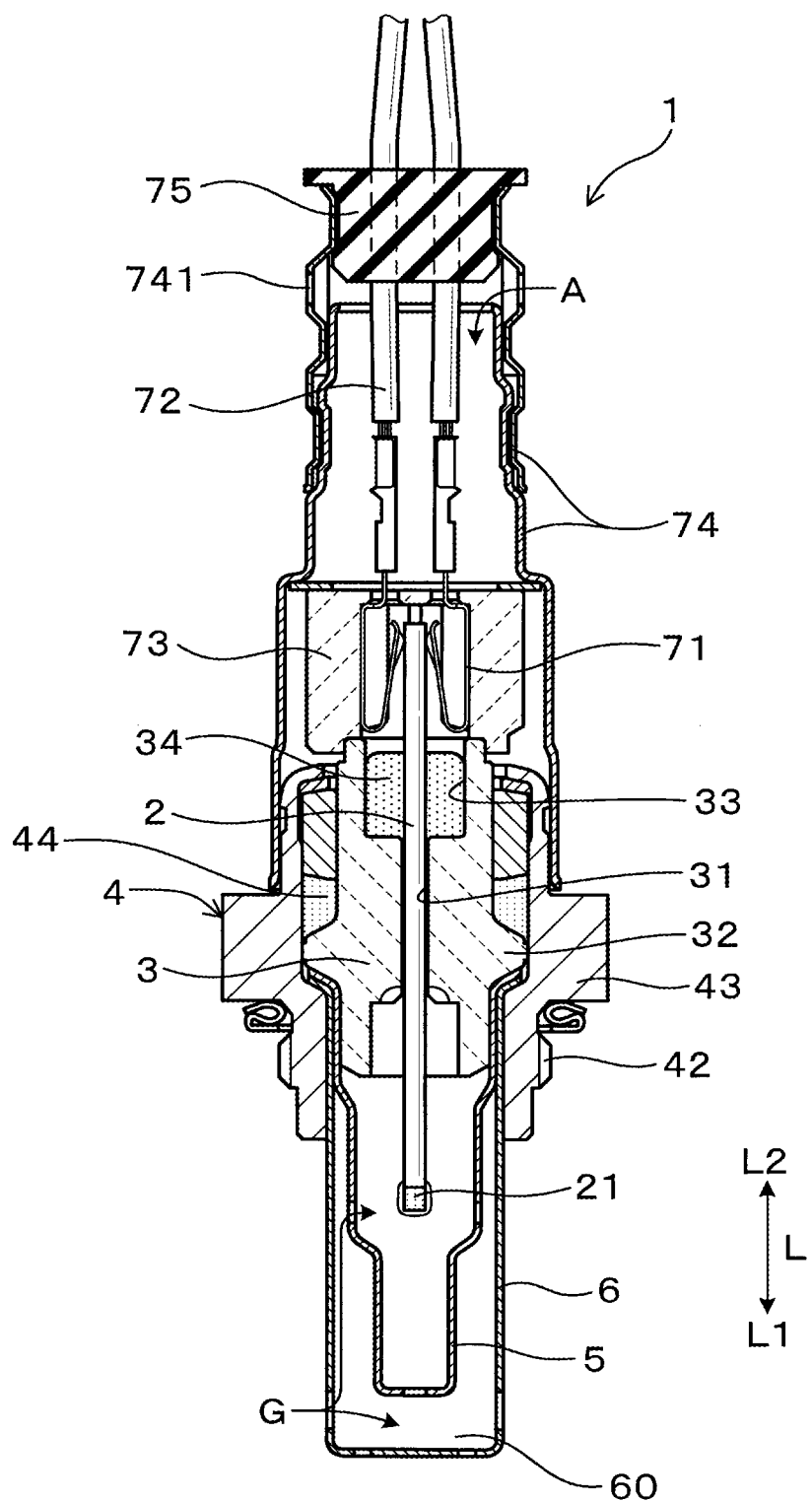
FIG. 1 is a cross-sectional view showing a gas sensor according to a first embodiment of the present disclosure.

As shown in FIG. 1, a gas sensor 1 according to the present embodiment is provided with a sensor element 2, an insulator 3, a housing 4, an inner cover 5 and an outer cover 6. The senor element 2 includes a detecting portion 21 that is exposed to detection gas G to perform gas detection. The insulator 3 is made of a ceramic material and holds the sensor element 2 in a state where the detecting portion 21 protrudes therefrom, the sensor element 2 being inserted through the insulator 3. The housing 4 is made of metal and disposed in the outer periphery of the insulator 3 and holds the insulator 3.

Figure 2:
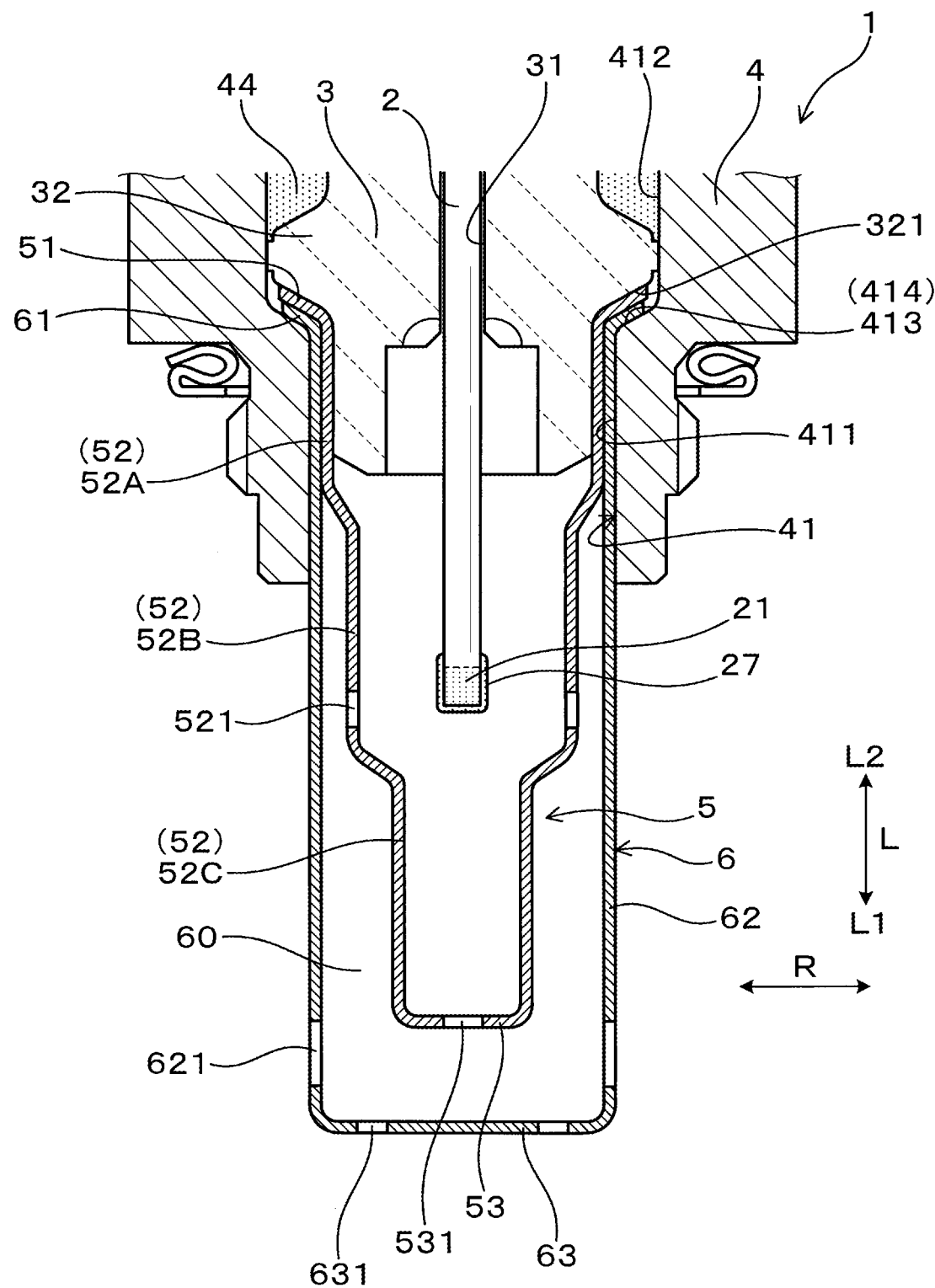
FIG. 2 is an enlarged cross-sectional view showing a part of the gas sensor according to the first embodiment.

As shown in FIG. 2, the inner cover 5 is made of metal material. The inner cover 5 covers the detecting portion 21 and has inner through holes 521 and 531. The outer cover 6 is made of metal material. The outer cover 6 covers the inner cover 5 so as to form a gas passage 60 through which the detection gas G flows, and has outer through holes 621 and 631.

Figure 3:
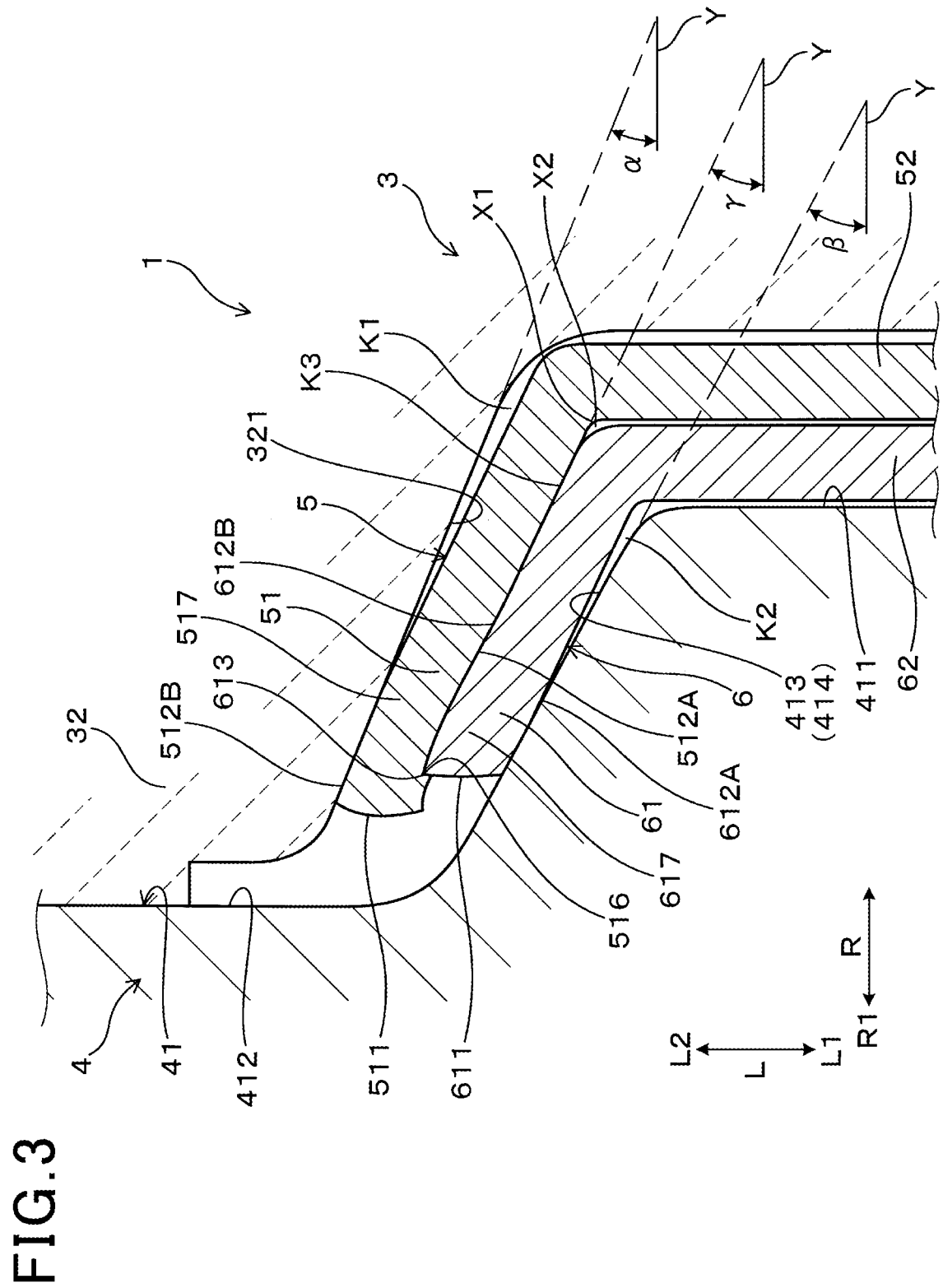
FIG. 3 is a cross-sectional view showing an inner flange portion and an outer flange portion supported between an insulator and a housing according to the first embodiment, as being enlarged in the peripheral portion thereof.

As shown in FIG. 3, an inner flange portion 51 formed in the entire circumference of the end portion of the inner cover 5, and an outer flange portion 61 formed in the entire circumference of the end portion of the outer cover 6 are supported between the insulator 3 and the housing 4. An end face 511 of the inner flange portion 51 and the end face 611 of the outer flange portion 611 are mutually displaced. According to the present embodiment, the end face 511 of the inner flange portion 51 is positioned in outer side R1 than the end face 611 of the outer flange portion 61. In the outer flange portion 61, a corner portion 613 between the end face 611 and a surface 612B is protruded into a surface 512A of the inner flange portion 512A.

According to the present embodiment, an insertion direction L is defined as a direction through which the sensor element 2 is inserted into the insulator 3. Also, a radial direction R is defined as a direction that orthogonally crosses the insertion direction L and radially extends from a central axis O that passes through the center of the sensor element 2 in the insertion direction L. Further, a direction around the central axis O is defined as a circumferential direction C. A tip end side L1 is defined as a side where the detecting portion 21 protrudes from the sensor element 2, and a rear end side L2 is defined as an opposite side of the tip end side L1.

Hereinafter, the detailed configuration of the gas sensor 1 according to the present embodiment will be described.

[Internal Combustion Engine]

The gas sensor 1 is disposed in a pipe of an exhaust system (i.e., exhaust pipe) of the internal combustion engine (engine) of a vehicle, and detects oxygen or specific gas in the detection gas G which is an exhaust gas that flows in the exhaust pipe. The gas sensor 1 can be disposed in an upper stream side in the exhaust pipe than a position at which the catalysis is disposed. Moreover, the gas sensor 1 can be disposed in a downstream side in the exhaust pipe than a position at which the catalysis is disposed. The exhaust pipe in which the gas sensor 1 is disposed can be an intake side pipe of the supercharger that increases the density of air drawn into the internal combustion engine by using the exhaust gas. The pipe in which the gas sensor 1 is disposed can be a pipe in the exhaust gas recirculation mechanism which recirculates a part of the exhaust gas exhausted to the exhaust passage from the internal combustion engine.

A vehicle provided with a pipe to which the gas sensor 1 is disposed may be an ordinal vehicle which travels with gas, a vehicle adapted for an idling stop, that is, a vehicle that stops the idling of the internal combustion engine when the vehicle is stopped, and a hybrid vehicle or the like. Also, the gas sensor 1 can be used for detecting the oxygen concentration of the exhaust gas from the internal combustion engine, detecting air-fuel ratio (A/F) of the internal combustion engine which is obtained from the exhaust gas, detecting whether the A/F obtained from the exhaust gas is in the fuel rich side or the fuel lean side relative to the theoretical A/F, and detecting specific gas component such as NOx.

[Sensor Element 2]

Figure 4:
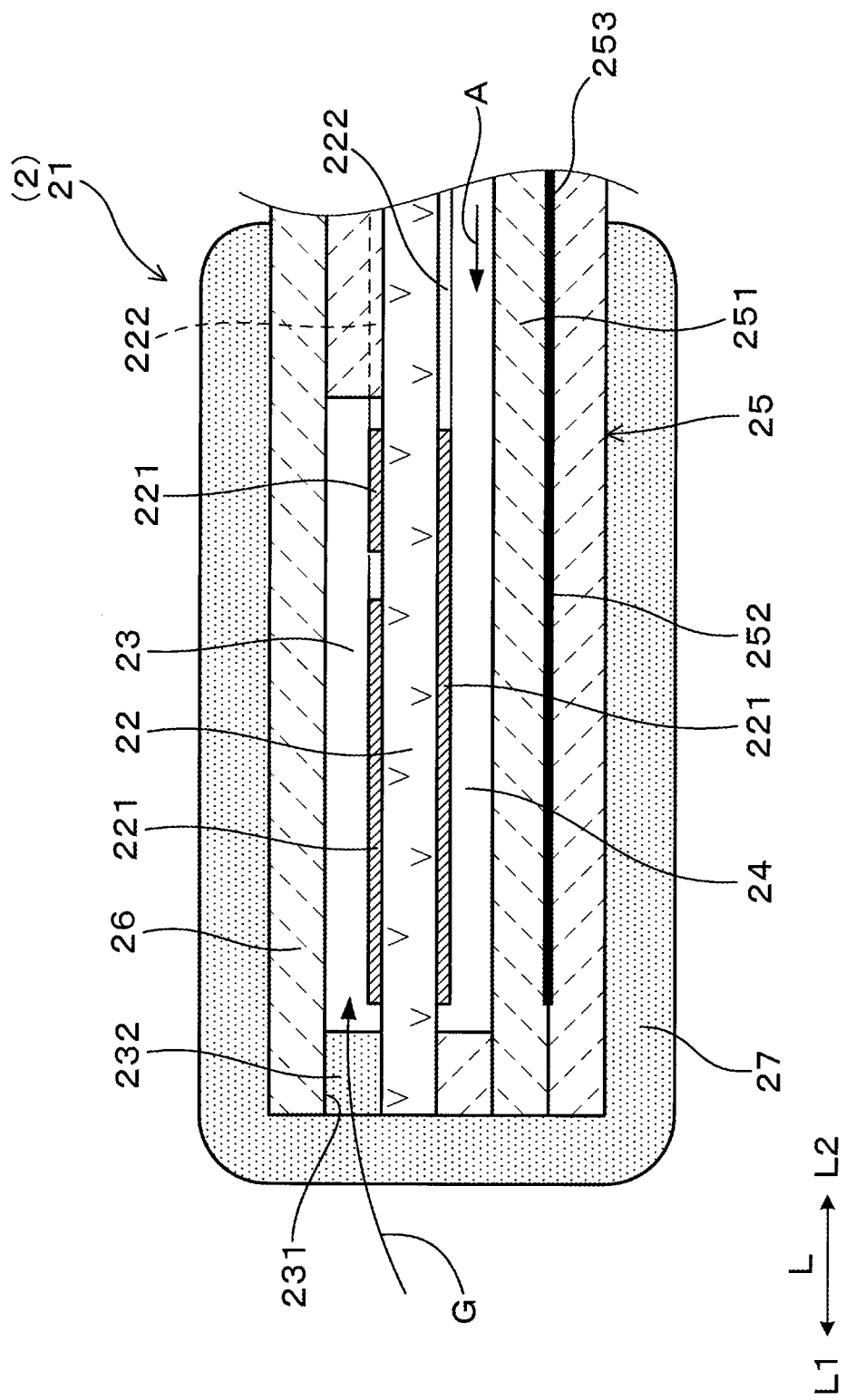
FIG. 4 is a cross-sectional view showing a detecting portion of a sensor element according to the first embodiment.
Figure 5:
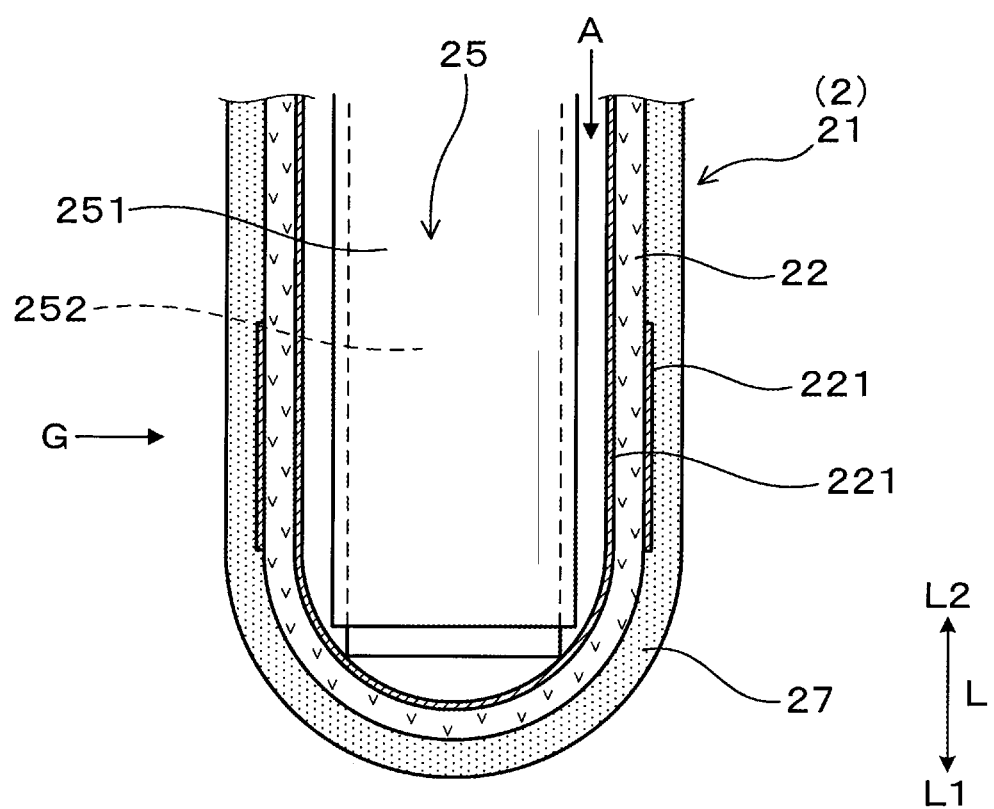
FIG. 5 is a cross-sectional view showing a detecting portion of other sensor element according to the first embodiment.

As shown in FIG. 4, the sensor element 2 incudes a solid electrolyte 22 having an ionic conductivity allowing oxide ion to be conducted in a predetermined activation temperature, a pair of electrodes 221 arranged on the surfaces of both sides of the solid electrolyte 22. The sensor element 2 according to the present embodiment is a laminate type element in which a plate-shaped heater 25 is laminated on the solid electrolyte 22 having a plate shape. The sensor element 2 may be constituted of a glass type element as shown in FIG. 5, in which a rod-shaped heater 25 is disposed in an inner periphery side of a glass-shaped electrolyte 22. In this case, the electrodes 221 is formed on the inner periphery and the outer periphery of the solid electrolyte 22.

The detection gas G is a target gas from which the gas detection is performed by a detecting portion 21 of the sensor element 2. That is, the detection gas G is an exhaust gas exhausted from the internal combustion engine. Note that atmospheric air is used as a reference gas A when performing the gas detection. According to the senor element 2 which is a laminate type element, the electrodes 221 to which the detection gas G touches (the electrodes 221 are exposed to the detection gas G) is formed on one surface of the plate-shaped electrolyte 22, and the electrodes 221 to which the reference gas A touches (the electrodes 221 are exposed to the reference gas A) is formed on the other surface of the plate-shaped electrolyte. According to the sensor element 2 which is a cup-shaped element, the electrodes 221 to which the detection gas G touches is formed on an outer surface of the glass-shaped electrolyte 22, and the electrode 221 to which the reference gas A touches is formed on an inner surface of the glass-shaped electrolyte 22. The heater 25 in each type of the sensor elements 2 includes a ceramic substrate 251, and a heating element 252 generating heat when being powered, which is disposed on the ceramic substrate 251.

As shown in FIGS. 1 and 2, the sensor element 2 is formed in a shape having the longitudinal side in the insertion direction L along which the sensor element 2 is inserted to the insulator 3. The detecting portion 21 of the sensor element 2 is provided at an end portion of the tip end side L1 in the insertion direction L of the sensor element 2 or in the vicinity of the end portion thereof. In the sensor element 2, a conductor portion 222 connected to the electrodes 221 and a conductor portion 253 connected to the heating element 252 are lead out from an end portion of the rear end side L2 in the insertion direction L. The electrodes 221 and the heating element 252 are connected to an external control circuit or the like via a connection terminal 71 and a lead wire 72.

As shown in FIG. 4, the detecting portion 21 is formed as a portion in which electrodes 221 are provided. The electrodes 221 exposed to the detection gas G are disposed in a gas chamber 23 which is surrounded by the ceramic substrate 26 having insulation properties laminated on the solid electrolyte 22. An introduction port 231 communicates with the gas chamber 23. The introduction port 231 includes a diffusion resistance layer 232 to introduce the detection gas G to the gas chamber 23 at a predetermined diffusion rate. A portion of the tip end side L1 in the insertion direction of the sensor element 2 is covered by a protection layer 27. The diffusion resistance layer 232 and the protection layer 27 are formed of a ceramic porous body. The sensor element 2 includes a duct 24 formed therein, the duct 24 introducing a reference gas A to the electrodes 221 exposed to the reference gas A. The duct 24 is formed, in the insertion direction L of the sensor element 2, from the end portion of the rear end side L2 to a position of the detecting portion 21 where the electrodes 221 are disposed.

[Other Sensor Element 2]

Figure 6:
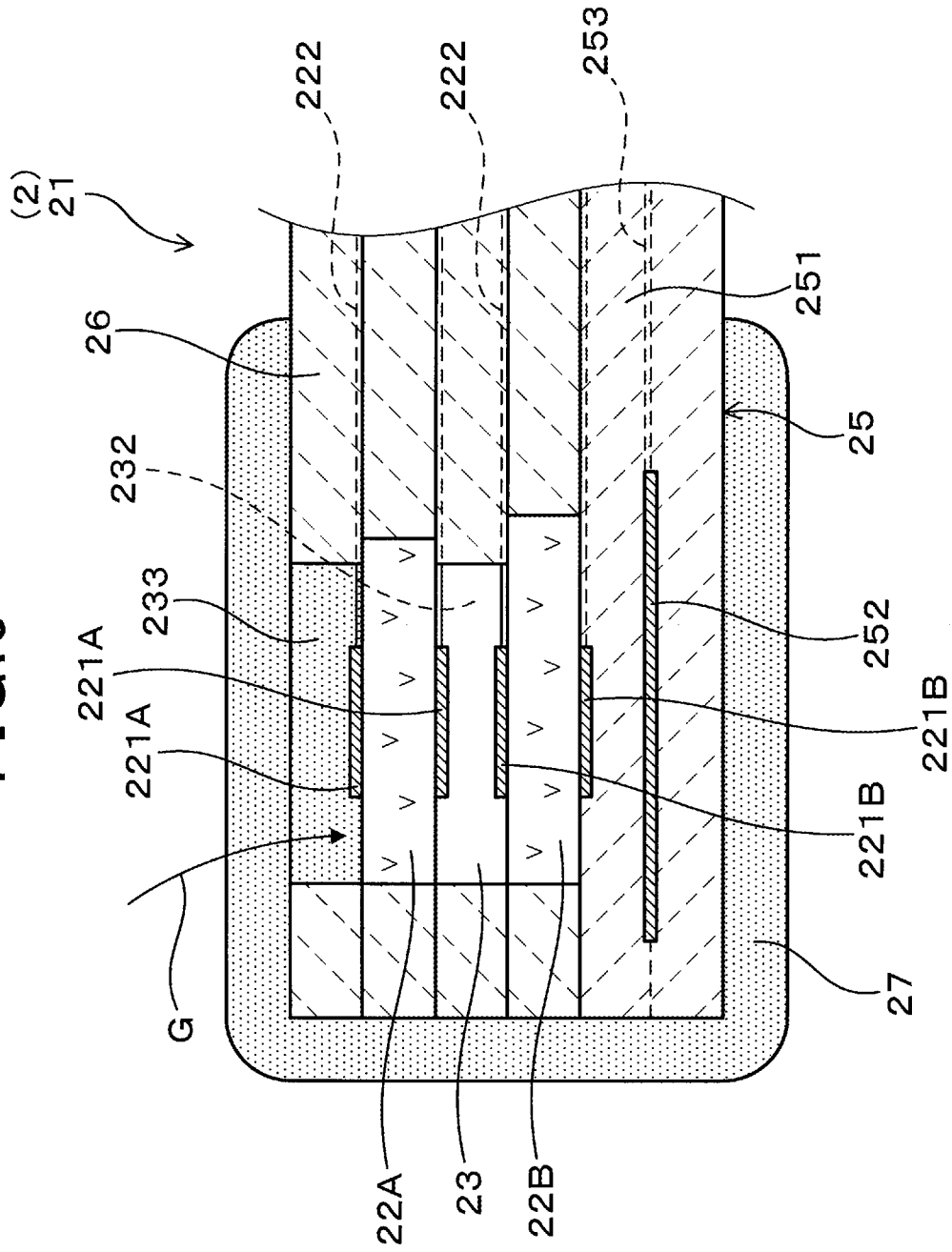
FIG. 6 is a cross-sectional view showing a detecting portion of other sensor element according to the first embodiment.

As shown in FIG. 6, the sensor element 2 can be formed by using two solid electrolytes 22A and 22B, in which a pair of electrodes 221 are provided to each of the solid electrolytes 22A and 22B. In this case, the gas chamber 23 is formed between the two solid electrolytes 22A and 22B to introduce the detection gas G. The gas chamber 23 is formed to be surrounded by the ceramic substrates 226 having insulation properties. A pair of pump electrodes 221A are formed on both sides of a first solid electrolyte 22A to adjust the oxygen concentration of the detection gas G in the gas chamber 23, the pump electrodes being provided to face each other via the first solid electrolyte 22A. One pump electrode 221A is disposed in the gas chamber 23 and the other pump electrode 221A is embedded to a gas introduction layer 233 formed of porous body through which the detection gas G permeate.

A pair of pump electrodes 221B are formed on both sides of a second solid electrolyte 22B to adjust the oxygen concentration of the detection gas G in the gas chamber 23, the pump electrodes 221B being provided to face each other via the second solid electrolyte 22B. One pump electrode 221B is disposed in the gas chamber 23 and the other pump electrode 221B is embedded to a ceramic substrate 251. Detection cell is formed by the pair of detection electrodes 221B and a part of the second solid electrolytes 22B disposed between the detection electrodes 221B. Also, the diffusion resistance layer 232 is provided in a position adjacent to the gas chamber 23, to introduce the detection gas G at a predetermined diffusion rate. The heater 25 is laminated on each of the solid electrolytes 22A and 22B. The heater 25 includes the ceramic substrate 251, and the heating element 252 provided in the ceramic substrate 251, generating heat when being powered.

[Insulator 3]

As shown in FIG. 1, the insulator 3 is made of a ceramic having insulation properties. The insulator 3 has an alignment hole 31 to place the sensor element 2 in the insulator 3. The alignment hole 31 penetrates the insulator 3 towards the insertion direction L. The sensor element 2 is inserted through the alignment hole 31 and fixed to the insulator 3 by a glass member 34 or the like which is filled in a concave portion 33 that communicates through the rear end side L2 of the alignment hole 31.

As shown in FIGS. 2 and 3, a support portion 32 is formed in the entire outer periphery of the insulator 3, which is supported in the inner periphery of the housing 4. An insulator opposing surface 321 that faces the inner flange portion 51 is formed on a surface in the tip end side L1 of the support portion 32. The insulator opposing surface 321 is formed to be inclined such that the position of the insulator opposing surface 321 with respect to the insertion direction L become closer to the rear end side L2, as the position of insulator opposing surface 321 with respect to the radial direction R become closer to the outer side R1 in the radial direction R.

In other words, the insulator opposing surface 321 has a tapered shape such that the diameter thereof increases towards the rear end side L2 from the tip end side L1 in the insertion direction L.

[Housing 4]

As shown in FIGS. 2 and 3, the housing 4 has a support hole 41 extending in the insertion direction L to dispose the insulator 3. The support hole 41 includes a small hole portion 411 positioned in the tip end side L1 in the insertion direction L, and a large hole portion 412 having a diameter larger than that of the small hold portion 411, positioned in the rear end side L2 in the insertion direction L2. The insulator 3 is inserted through the small hole portion 411 and the large hole portion 412 of the support hole 41, and fixed to the housing 4 by bending the end portion of the housing 4 in the rear end side L2 in the insertion direction L, using talc powder and a sealing member 44 such as sleeve seal provided in the large hole portion 412.

A step portion 413 is formed in the entire circumference space between the small hole portion 411 and the large hole portion 412. The step portion 413 has a housing opposing surface 414 that faces the outer flange portion 61. The housing opposing surface 414 is formed to be inclined such that the position of the housing opposing surface 414 with respect to the insertion direction L become closer to the rear end side L2, as the position of the housing opposing surface 414 with respect to the radial direction R become closer to the outer side R1 in the radial direction R. In other words, the housing opposing surface 414 has a tapered shape such that the diameter thereof increases towards the rear end side L2 from the tip end side L1 in the insertion direction L. Also, as shown in FIG. 1, a screw portion 42 and a flange portion 43 are formed on the entire outer periphery of the housing 4 so as to mount the gas sensor 1 which is inserted into a mount hole provided to the pipe.

[Rear End Side Insulator 73]

As shown in FIG. 1, a rear end side insulator 73 is disposed in the rear end side L2 of the insulator 3 in the insertion direction L, thereby supporting the connection terminal 71 which is electrically connected to the conductor portion 222 of the electrodes 221 or the conductor portion 253 of the heating element 252. Further, in the housing 4, a wiring cover 74 is disposed in a portion closer to the rear end side L2 than the flange portion 43 in the insertion direction L, to cover the rear end side insulator 73, the connection terminal 71 and the lead wire 72 or the like. The lead wire 72 is supported by a bush 75 disposed in the wiring cover 74. The wiring cover 74 has an introduction port 741 formed therein, for introducing atmospheric air as the reference gas A. The atmospheric air introduced from the introduction port 741 is lead to the duct 24 of the sensor element 2 through the gap in the wiring cover 74 and the rear end side insulator 73.

[Inner Cover 5 and Outer Cover 6]

As shown in FIG. 2, the inner cover 5 includes an inner cylindrical portion 52 formed in a cylindrical shape along the insertion direction L, and an inner bottom portion 53 formed at an end portion of the inner cylindrical portion 52 in the tip end side L1 in the insertion direction L. For the inner through holes 521 and 531 through which the detection gas G passes, a plurality of inner through holes 521 are formed at plural positions of the inner cylindrical portion 52 in the circumferential direction C, the inner through hole 531 is formed at the inner bottom portion 53. The inner cylindrical portion 52 includes a first inner cylindrical portion 52A attached to the outer periphery of the insulator 3, a second inner cylindrical portion 52B being extended from the tip end side of the first inner cylindrical portion 52A in the insertion direction L, having smaller diameter than that of the first inner cylindrical portion 52A, and a third inner cylindrical portion 52C being extended from the tip end side of the second inner cylindrical portion 52B in the insertion direction L, having smaller diameter than that of the second inner cylindrical portion 52B. The detecting portion 21 of the sensor element 2 is disposed in the second inner cylindrical portion 52B.

The inner flange portion 51 is formed in the rear end portion of the first inner cylindrical portion 52A in the insertion direction L such that the inner flange portion 51 is bent towards the outer side R1 in the radial direction R. The inner flange portion 51 is formed to be inclined such that the position of inner flange portion 51 with respect to the insertion direction L become closer to the rear end side L2, as the position of the inner flange portion 51 with respect to the radial direction R become closer to the outer side R1 in the radial direction R. In other words, the inner flange portion 51 has a tapered shape such that the diameter thereof increases towards the rear end side L2 from the tip end side L1 in the insertion direction L.

The outer cover 6 includes an outer cylindrical portion 62 formed in a cylindrical shape along the insertion direction L, and an outer bottom portion 63 formed in an end portion of the outer cylindrical portion 62 in the insertion direction L. For the outer through holes 621 and 631 through which the detection gas G passes, a plurality of outer through holes 621 are formed at plural positions of the outer cylindrical portion 62 in the circumferential direction C, and a plurality of inner through holes 631 are formed at plural positions of the outer bottom portion 63.

The outer flange portion 61 is formed in the rear end portion of the outer cylindrical portion 62 in the insertion direction L such that the outer flange portion 61 is bent towards the outer side R1 in the radial direction R. The outer flange portion 61 is formed to be inclined such that the position of outer flange portion 61 with respect to the insertion direction L become closer to the rear end side L2, as the position of the outer flange portion 61 with respect to the radial direction R become closer to the outer side R1 in the radial direction R. In other words, the outer flange portion 61 has a tapered shape such that the diameter thereof increases towards the rear end side L2 from the tip end side L1 in the insertion direction L.

As shown in FIG. 2, the gas passage 60 between the inner cover 5 and the outer cover 6 is formed continuously between the inner cylindrical portion 52 of the inner cover 5 and the outer cylindrical portion 62 of the outer cover 6, and the inner bottom portion 53 of the inner cover 5 and the outer bottom portion 63 of the outer cover 6. A part of the detection gas G flowing from the pipe of the internal combustion flows inside the outer cover 6 by passing through the outer through holes 621 and 631, and flows inside the inner cover 5 by passing through the gas passage 60 and the inner through holes 521. Then, this detection gas G contacts the detecting portion 21 of the sensor element 2 inside the inner cover 5, and flows into the gas passage 60 by passing through the inner through hole 531 from inside the inner cover 5. Further, the detection gas G flows outside the outer cover 6 by passing the outer through holes 621 and 631 from the gas passage 60.

The inner cover 5 and the outer cover 6 are arranged in the pipe, whereby the detection gas G may flow into a gap formed between the support hole 41 of the housing 4 and the outer cylindrical portion 62 of the outer cover 6, a gap between the outer cylindrical portion 62 of the outer cover 6 and the inner cylindrical portion 52 of the inner cover 5, and a gap between the inner cylindrical portion 52 of the inner cover 5 and the outer periphery of the insulator 3. Also, the pressure inside the pipe is higher than the atmospheric pressure. Hence, by keeping air tightness at the inner flange portion 51 and the outer flange portion 61 which are positioned (supported) between the insulator opposing surface 321 and the housing opposing surface 414, the detection gas G flowing into the respective gaps can be prevented from deeply entering inside the support hole 41, and also prevented from being mixed with the atmospheric air as the reference gas A that flows through the duct 24 of the sensor element 2.

The inner cover 5 and the outer cover 6 are formed of stainless steel having fine corrosion resistance. The inner cover 5 and the outer cover 6 according to the present embodiment is formed of SUS310S. When using the same material for the inner cover 5 and the outer cover 6, since electrical properties are the same between the inner cover 5 and the inner cover 6, potential difference is unlikely to occur therebetween. Hence, the corrosiveness of these materials can be improved. For the inner cover 5 and the outer cover 6, a metal material having good corrosiveness other than the stainless steel can be used.

The materials for the inner cover 5 and the outer cover 6 may be the same or different. When these materials are different from each other, the rigidity of a cover to which the corner portion is protruded can be lowered compared to the rigidity of a cover in which the corner portion protrudes into the other cover. In this case, intrusion of the corner portion can readily be accomplished. However, when the rigidities due to the difference of the materials are not so different, the rigidity of a cover to which the corner portion is protruded can be higher than that of a cover in which the corner portion protrudes into the other cover.

[Inner Flange Portion 51 and Outer Flange Portion 61]

As shown in FIG. 2, the inner through hole 521 of the inner cylindrical portion 52 and the outer through hole 621 of the outer cylindrical portion 62 are formed to be offset each other in the insertion direction L. The inner through hole 531 of the inner bottom portion 53 and the outer through hole 631 of the outer bottom portion 63 are offset each other in the radial direction R. The first inner cylindrical portion 52A of the inner cylindrical portion 52, positioned in the rear end side L2 in the insertion direction L, is disposed to overlap the inner periphery side of the outer cylindrical portion 62 in the rear end side L2 in the insertion direction L. The inner flange portion 51 is disposed to overlap the rear end side L2 of the outer flange portion 61 in the insertion direction L.

As shown in FIG. 3, the length from a bending point X1 in the outer periphery side of the inner flange portion 51, which bends from the inner cylindrical portion 52, to the end face 511 is longer than a length from a bending point X2 in the inner periphery side of the outer cylindrical portion 62, which is bending from the outer cylindrical portion 62, to the end face 611. The end face 511 of the inner flange portion 51 is positioned in the outer side R1 with respect to the radial direction R, compared to the end face 611 of the outer flange portion 61.

Here, the bending point X1 refers to a point at which a virtual line drawn along the outer periphery surface of the inner cylindrical portion 52 in the insertion direction L, and a virtual line drawn along the surface 512A in the tip end side L1 of the inner flange portion 51 cross each other, in a cross section of the inner cover 5 and the outer cover 6 taken along the insertion direction L. The bending point X2 refers to a point at which a virtual line drawn along the inner periphery surface of the outer cylindrical portion 62 in the insertion direction L, and a virtual line drawn along the surface 612B in the rear end side L2 of the outer flange portion 61 are crossed each other, in a cross section of the inner cover 5 and the outer cover 6 taken along the insertion direction L.

According to the present embodiment, the corner portion 613 formed between the end face 611 and the surface 612B in the rear end side L2 in the insertion direction L is protruded into the surface 512A in the tip end side L1 in the insertion direction L. A depression part 516 caused by the intrusion of the corner portion 613 is formed on the surface 512A of the inner flange portion 51. The end face 511 of the inner flange portion 51 refers to a tip end face positioned in the outer side R1 of the inner flange portion 51 with respect to the radial direction R. The end face 611 of the outer flange portion 61 refers to a tip end face positioned in the outer side R1 of the outer flange portion 61 with respect to the radial direction R.

The thickness of the outer flange portion 61 and the inner flange portion 51 may preferably be within a range from 0.2 mm to 2.0 mm. In the case where the thickness is less than 0.2 mm, the strength of the outer flange portion 61 or the inner flange portion 51 is insufficient. On the other hand, when the thickness is larger than 2.0 mm, a pressing or the like for the outer flange portion or the inner flange portion is difficult to achieve.

Also, an amount by which the corner portion 613 of the outer flange portion 61 protrudes into the surface 512A of the inner flange portion 613 may preferably be in a range from 0.01 mm to 1.8 mm. When the amount of intrusion is less than 0.01 mm, air tightness between the insulator 3 and the housing 4 is difficult to be secured. When the amount of intrusion is larger than 1.8 mm, force is required to increase for putting the inner flange portion 51 and the outer flange portion 61 between the insulator 3 and the housing 4. This is not favorable when assembling the gas sensor 1 to the pipe.

Regarding the position of intrusion where the corner portion 613 of the outer flange portion 61 protrudes into the surface 512A of the inner flange portion 51, a position may preferably be located in a range from 0.1 mm to 5.0 mm, from the end face 511 of the inner flange portion 511 towards the inner periphery side along the surface 512A in the tip end side L1 of the inner flange portion 51 in the insertion direction L. The distance of the intrusion is set as the same as a distance between the end face 511 of the inner flange portion 51 to the end face 611 of the outer flange portion 61. In the case where the position of the intrusion is less than 0.1 mm, it is difficult for the corner portion 613 to protrude into the surface 512. On the other hand, when the position of the intrusion is larger than 5.0 mm, the end face 511 of the inner flange portion 51 and the end face 611 of the outer flange portion are positioned significantly apart from each other. Accordingly, either the inner flange portion 51 or the outer flange portion 61 has to be formed to be significantly shorter than the others. This is inappropriate.

Figure 7:
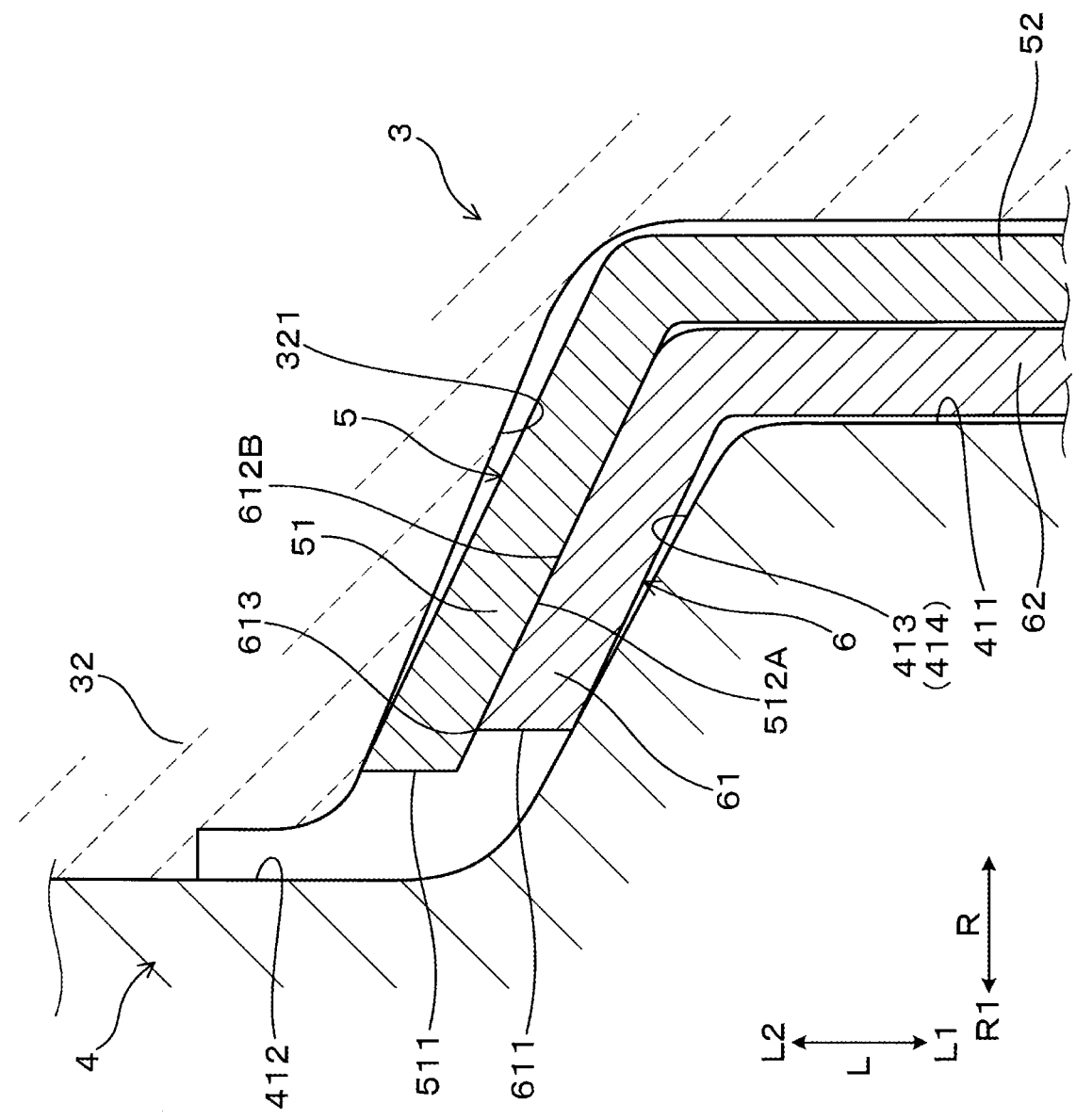
FIG. 7 is a cross-sectional view showing the inner flange portion and the outer flange portion before being supported between the insulator and the housing according to the first embodiment, as being enlarged in the peripheral portion thereof.

As shown in FIG. 7, in an initial state of the inner cover 5 and the outer cover 6 before assembling the gas sensor 1, the end face 511 of the inner flange portion 51 is formed approximately parallel to the insertion direction L, and also the end face 611 of the outer flange portion 61 is formed approximately parallel to the insertion direction L. In the initial state, the corner portion 613 in the outer flange portion 61, formed between the end face 611 and the surface 612B in the rear end side L2 in the insertion direction L, is formed in an acute shape. The corner portion 613 is formed in the acute shape, whereby the corner portion 613 is likely to protrude into the surface 512A of the inner flange portion 51 in the tip end side L1 in the insertion direction L. Note that the corner portion 613 is kept in the acute shape even after assembling the gas sensor 1.

The end face 511 of the inner flange portion 51 can be formed to be in approximately parallel to the insertion direction L, by cutting a portion to be formed as the inner flange portion 51 in the insertion direction L, after shaping the inner cover 5 by a drawing or the like. Similarly, the end face 611 of the outer flange portion 61 can be formed to be in approximately parallel to the insertion direction L, by cutting a portion to be formed as the inner flange portion 61 in the insertion direction L, after shaping the outer cover 6 by drawing or the like.

When the inner flange portion 51 and the outer flange portion 61 are disposed between the insulator opposing surface 321 and the housing opposing surface 414, the end portion of the inner flange portion 51 and the end face of the outer flange portion 61 are plastically deformed. After assembling the gas sensor 1, the end face 511 of the inner flange portion 51 and the end face 611 of the outer flange portion 61 may be inclined with respect to the insertion direction L, or may be bent to have curved surface.

The end face 511 of the inner flange portion 51 may be formed in a direction substantially orthogonal to a direction along which the inner flange portion 51 is formed. Also, the end face 511 of the inner flange portion 51 is not necessary to be formed in a flat shape, but may be formed in a curved surface shape having convex or concave shape, an uneven shape, and a shape in which a part of shape is expanded. Similarly, the configuration of the end face 611 of the outer flange portion 51 is the same as that of the end face 511 of the inner flange portion 51.

[Other Inner Flange Portion 51 and Outer Flange Portion 61]

Figure 8:
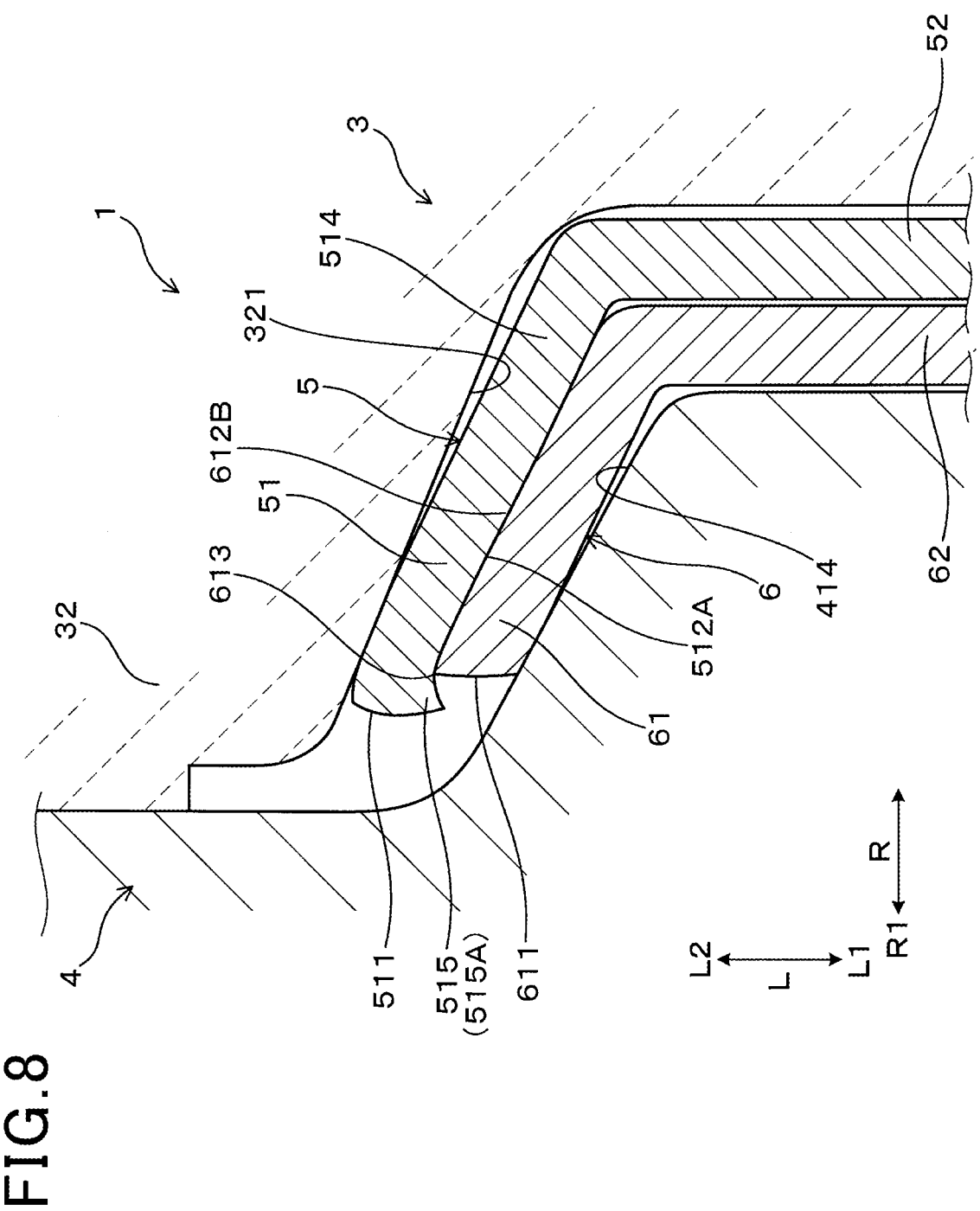
FIG. 8 is a cross-sectional view showing other inner flange portion and outer flange portion supported between the insulator and the housing according to the first embodiment, as being enlarged in the peripheral portion thereof.

A relationship of the engagement between the inner flange portion 51 and the outer flange portion 61 may be in the following way. Instead of intruding the corner portion 613 of the outer flange portion 61 into the surface 512A of the inner flange portion 51, as shown in FIG. 8, the end portion of the inner flange portion 51 may be bent to overhang the corner portion 613 between the end face 611 and the surface 612B in the rear end side L2 of the insertion direction L. In this case, a bend portion 515A is formed at the end portion 515 in the inner flange portion 51, which is bent with respect to a body 514 connected to the inner cylindrical portion 52. Further, in this case, a portion at the bend portion 515A of the inner flange portion 51, which is around the bend portion in the tip end side L1 in the insertion direction L, contacts to the tip end of the corner portion 613 of the outer flange portion 61.

[Inclination Angle $\alpha$, $\beta$, $\gamma$]

As shown in FIG. 3, according to the gas sensor 1 of the present embodiment, the inclination angles $\alpha$, $\beta$, $\gamma$ respective portions of the insulator 3 and the housing 4 which supports the inner flange portion 51 and the outer flange portion 61 are appropriately considered.

Specifically, the inclination angles $\alpha$, $\beta$, $\gamma$ are formed to be different from each other. That is, the inclination angle $\alpha$ of the insulator opposing surface 321 in the support portion 32 of the insulator 3, with respect to a virtual reference line Y which is parallel to the radial direction; the inclination angle $\beta$ of the housing opposing surface 141 formed at the step portion 413 in the support hole 41 of the housing 4, with respect to a virtual reference line Y which is parallel to the radial direction R; and the inclination angle $\gamma$ of the inner flange portion 51 and the outer flange portion 61, with respect to a virtual reference line Y which is parallel to the radial direction R, are different. Note that inclination angles $\alpha$, $\beta$, $\gamma$ are slightly different from each other, however, the difference among the inclination angles $\alpha$, $\beta$, $\gamma$ are illustrated with exaggeration.

According to the present embodiment, the inclination angle $\gamma$ of the inner flange portion 51 and the outer flange portion 61 is larger than the inclination angle $\alpha$ of the insulator opposing surface 321, and smaller than or equal to the inclination angle $\beta$ of the housing opposing surface 414. In other words, a relationship $\alpha<\gamma\leq\beta$ is satisfied according to the gas sensor 1 of the present embodiment. With this configuration, the surface 512B in the rear end side L2 of the end portion of the inner flange portion 51 is likely to contact the insulator opposing surface 321, and the surface 612A in the tip end side L1 of the end portion of the outer flange portion 61 is likely to contact the housing opposing surface 414. A large amount of load can be applied between the corner portion 613 of the outer flange portion 61 and the surface 512A of the inner flange portion 51, so that the corner portion 613 of the outer flange portion 61 can be protruded into the surface 512A. As a result, air tightness between the inner flange portion 51 and the outer flange portion 61 can be improved.

Since the inclination angle α of the insulator opposing surface 321 is smaller than the inclination angle β of the housing opposing surface 414, a gap can be formed between the insulator opposing surface 321 and the housing opposing 414 such that the closer to the outer side R1 of the radial direction R, the smaller the gap is. Thus, with the insulator opposing surface 321 and the housing opposing surface 414, the outer periphery side portion 517 of the inner flange portion 51, and the outer periphery side portion 617 of the outer flange portion 61 can readily be pressurized. Hence, the end portion 613 of the outer flange portion 61 is likely to protrude into the surface 512A of the inner flange portion 51, or the end portion of the inner flange portion 51 is likely to be deformed.

The inclination angle γ of the inner flange portion 51 and the outer flange portion 61 is set between the inclination angle α of the insulator opposing surface 321 and the inclination angle β of the housing opposing surface 414, thereby producing a state where the outer periphery side portion 517 of the inner flange portion 51 and the outer periphery side portion 617 of the outer flange portion 617 are likely to be compressed.

In the gas sensor 1, instead of satisfying the relationship α<γ≤β, a relationship α≤γ<β may be satisfied. This is achieved under a condition that the inclination angle α of the insulator opposing surface 321 is smaller than the inclination angle β of the housing opposing surface 414, and the inclination angle γ of the inner flange portion and the outer flange portion 61 may be the same as the inclination angle α of the insulator opposing surface 321 or the inclination angle β of the housing opposing surface 414. At least when the inclination angle α of the insulator opposing surface 321 is smaller than the inclination angle β of the housing opposing surface 414, the following effects can be obtained. That is, the corner portion 613 of the outer flange portion 61 is likely to protrude into the surface 512A of the inner flange portion 51, or the end portion of the inner flange portion 51 is likely to be deformed.

A difference between the inclination angle α of the insulator opposing surface 321 and the inclination angle β of the housing opposing surface 414 can be set within a range from 0.5° to 10°. In the case where the difference between the inclination angle α and the inclination angle β is small, it is difficult to obtain an effect where the corner portion 613 is likely to protrude into the surface 512A. On the other hand, when the difference between the inclination angle α and the inclination angle β is significantly large, a contact area between the insulator 3, the inner flange portion 51, the outer flange portion 61 and the housing 4 becomes small.

The insulator opposing surface 321 and the opposing surface 414 are appropriately inclined so that appropriate shearing load in addition to a compressive load can be applied between the inner flange portion 51 and the outer flange portion 61. Hence, adhesion strength between the insulator 3, the inner flange portion 51, the outer flange portion 61 and the housing 4 can be enhanced. Each of the inclination angle α of the insulator opposing surface 321, the inclination angle β of the housing opposing surface 414, and the inclination angle γ of the outer flange portion 61 can be set within a range from 5° to 45°, on the assumption that a relationship α<γ≤β, or a relationship α≤γ<β is satisfied.

When respective inclination angles α, β, γ are significantly small, the enhanced adhesion effect is unlikely to be obtained between the insulator 3, the inner flange portion 51, the outer flange portion 61 and the housing 4. Meanwhile, when the respective inclination angles α, β, γ are significantly large, the inner flange portion 51 and the outer flange portion 61 are difficult to support between the insulator opposing surface 321 and the housing opposing surface 414.

Moreover, after assembling the gas sensor 1, the inner flange portion 51 and the outer flange portion 61 are closely contacted with each other. Before assembling the gas sensor 1, the inclination angle γ of the inner flange portion 51 and the inclination angle γ are configured to be the same. However, the inclination angle γ of the inner flange portion 51 and the inclination angle γ may be different, before assembling the gas sensor 1. In this case, since the inner flange portion 51 and the outer flange portion 61 are closely contacted with each other, when being supported between the insulator opposing surface 321 and the housing opposing surface 414, the inclination angle γ of the inner flange portion 51 and the inclination angle γ of the outer flange portion become the same.

Depending on the length of the inner flange portion 51 and the outer flange portion 61, a thickness relationship, a relationship between the inclination angles α, β, γ or the like, as shown FIG. 8, the end portion of the inner flange portion 51 may be bent towards the end face 611 of the outer flange portion 61, when the inner flange portion 51 and the outer flange portion 61 are supported between the insulator opposing surface 321 and the housing opposing surface 414. In this case, the end portion of the inner flange portion may be positioned (bent) to overhang the corner portion 613 of the outer flange portion 61.

[Alignment of Positional Offset]

Figure 9:
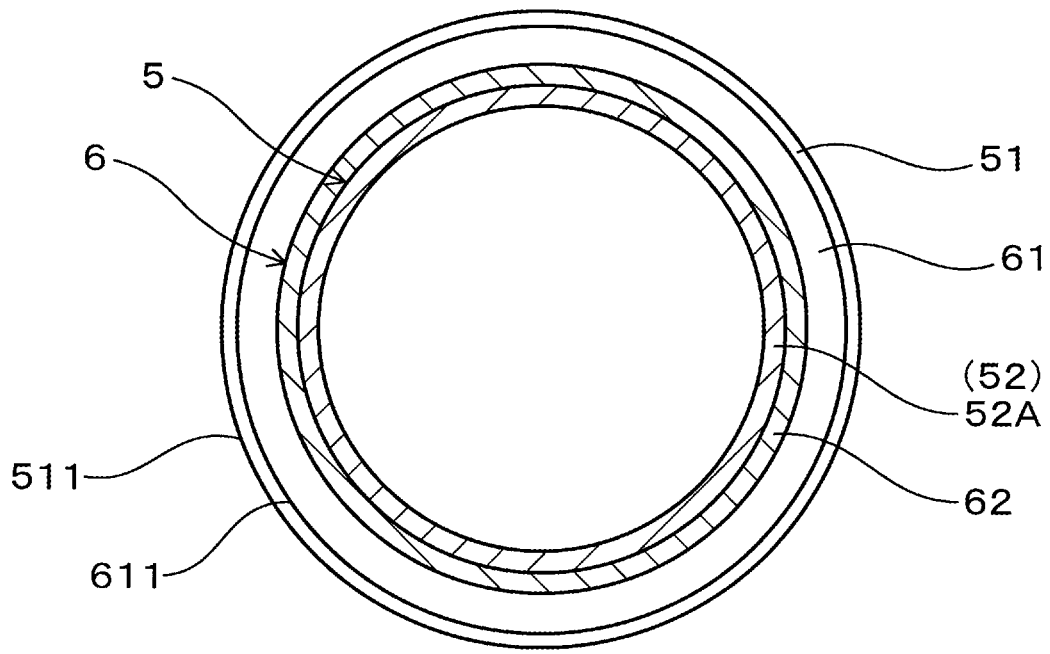
FIG. 9 is an explanatory diagram showing the inner flange portion and the outer flange portion according to the first embodiment, when seen from a tip end portion of the sensor element in the insertion direction thereof.

As shown in FIG. 9, according to the present embodiment, mutual positions between the end face 511 of the inner flange portion 51 and the end face 611 of the outer flange portion 61 are offset such that the end face 511 of the entire periphery in the circumferential direction C of the inner flange portion 51 is positioned to be in the outer side R1 than the end face 611 of the entire periphery in the circumferential direction C of the outer flange portion 61. In other words, the positional offset is accomplished such that the center axis line of the inner cover 5 passing through the center of the inner cylindrical portion 52 and the inner bottom portion 53 in the insertion direction L, and the center axis line of the outer cover 6 passing through the center of the outer cylindrical portion 62 and the outer bottom portion 63 are coincident, and the length of the inner flange portion 51 is longer than that of the outer flange portion 61 over the entire periphery in the circumferential direction C.

Figure 10:
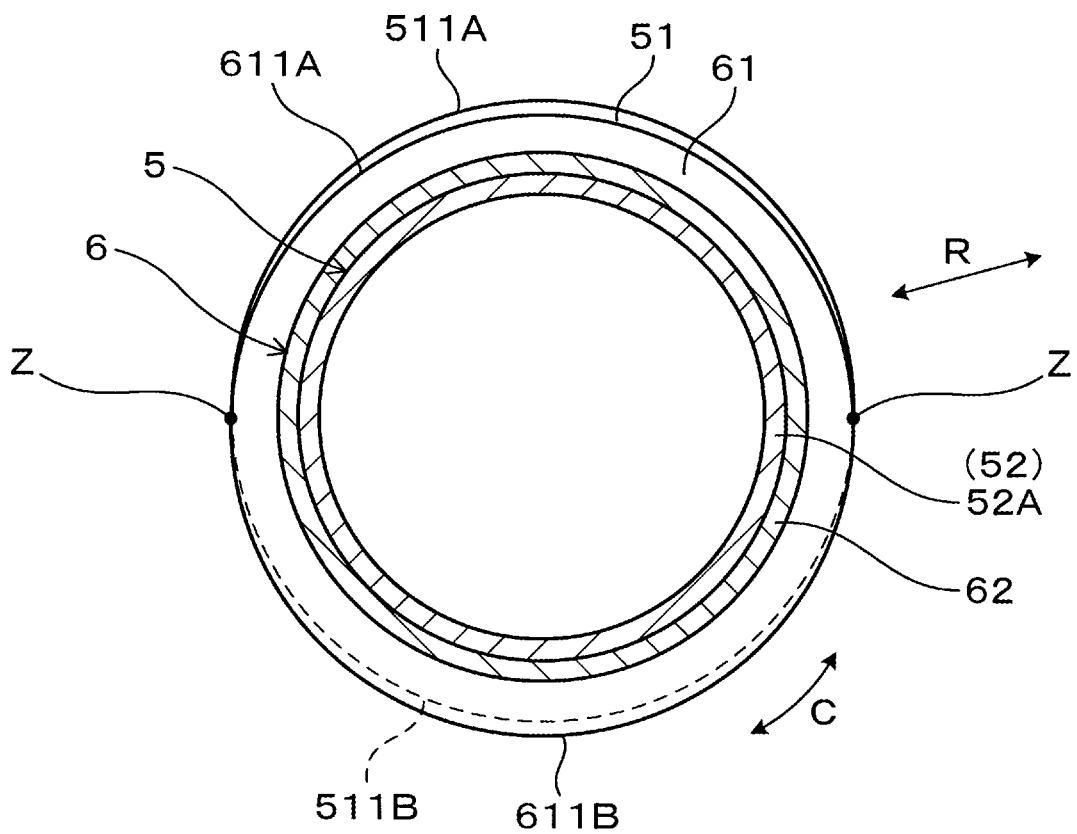
FIG. 10 is an explanatory diagram showing another inner flange portion and outer flange portion according to the first embodiment, when seen from a tip end portion of the sensor element in the insertion direction thereof.

Other than this, as shown in FIG. 10, the mutual positions between the end face 511 of the inner flange portion 51 and the end face 611 of the outer flange portion 61 can be aligned such that the center axis line of the inner cover 5 and the outer cover 6 are slightly eccentrically positioned, although the lengths of the inner flange portion 51 and the outer flange portion 61 are the same. In this case, the end face 511A of the inner flange portion 51, corresponding to half of the periphery in the circumferential direction C is positioned radially (with respect to the radial direction R) towards outer side R1 than the position of the end face 611A of the outer flange portion, corresponding to half of the periphery in the circumferential direction C, and the end face 5116 of the inner flange portion 51, corresponding to rest of the half periphery in the circumferential direction C is positioned radially (with respect to the radial direction R) towards inner side than the end face 611B of the outer flange portion 61, corresponding to rest of the half periphery in the circumferential direction C.

Also, in the half periphery portion of the inner flange portion 51 and the outer flange portion 61, the length of the inner flange portion 51 may be longer than the length of the outer flange portion 61, whereby the end face 511A of the inner flange portion 51 may be positioned radially toward outer periphery side than the position of the end face 611A of the outer flange portion 61. In this case, in the rest of the half periphery portion of the inner flange portion 51 and the outer flange portion 61, the length of the inner flange portion 51 may be shorter than the length of the outer flange portion 61, whereby the end face 5116 of the inner flange portion 51 may be positioned radially toward inner periphery side than the position of the end face 611B of the outer flange portion 61.

Moreover, as shown in FIG. 10, portions Z are formed at two positions of the inner flange portion 51 and the outer flange portion 61 in the circumferential direction C, where a position of the end face 511 in the radial direction R of the inner flange portion 51 and a position of the end face 611 in the radial direction R of the outer flange portion 61 are overlapped. In this case, a gap at a boundary part between the inner flange portion 51 and the outer flange portion 61, which is likely to be formed at the overlapped portion Z, becomes minimal. Accordingly, this does not affect an effect of maintaining the air tightness between the insulator 3 and the housing 4.

[Other Gas Sensor 1]

Figure 11:
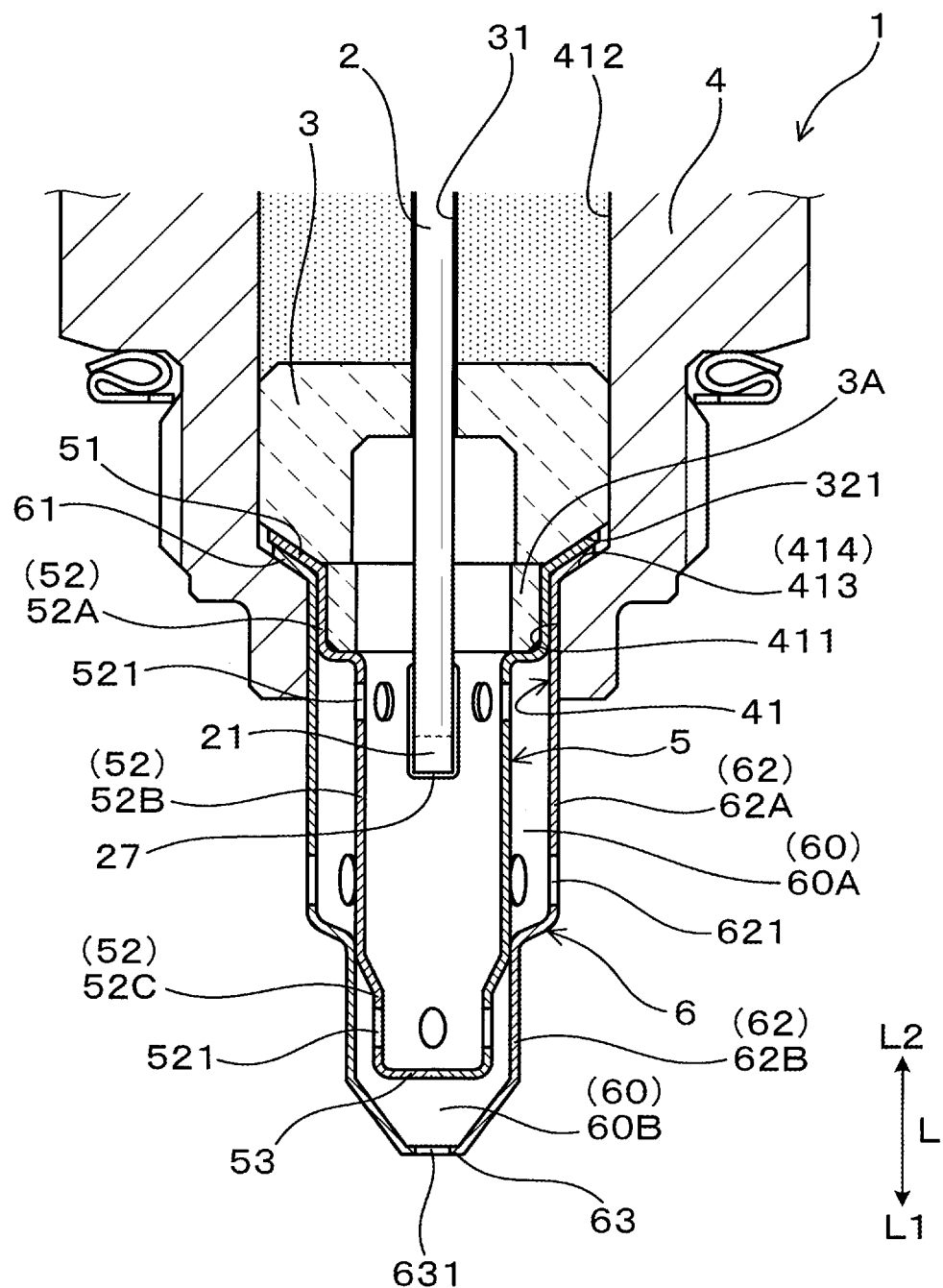
FIG. 11 is a cross-sectional view showing other gas sensor according to the first embodiment, as being enlarged in a part thereof.

As shown in FIG. 11, according to other gas sensor 1, the gas passage 60 between the inner cover 5 and the outer cover 6 may be formed to be divided into two passages such that the inner cylindrical portion 52 of the inner cover 5 and the outer cylindrical portion 62 of the outer cover 6 are contacted with each other not only in the rear end side L2 in the insertion direction L but also in the tip end side L1 in the insertion direction.

In this case, the outer cylindrical portion 62 of the outer cover 6 is provided with a rear end outer cylindrical portion 62A positioned in the rear end side L2 of the insertion direction L, and a tip end outer cylindrical portion 62B connected to the tip end side L1 of the rear end outer cylindrical portion 62A, having smaller diameter than that of the rear end outer cylindrical portion 62A. The inner cylindrical portion 52 of the inner cover 5 includes a first inner cylindrical portion 52A, a second inner cylindrical portion, and a third inner cylindrical portion 52C. The first inner cylindrical portion 52A is attached to the outer periphery of the tip end side insulator 3A which is adjacent to the tip end side L1 of the insulator 3 in the insertion direction. The second inner cylindrical portion 52B is connected to the tip end side L1 of the first inner cylindrical portion 52A in the insertion direction L, having smaller diameter than that of the first inner cylindrical portion 52A. The third inner cylindrical portion 52C is connected to the tip end side L1 of the second inner cylindrical portion 52B in the insertion direction L, having smaller diameter than that of the second inner cylindrical portion 52B.

The rear end portion of the tip end outer cylindrical portion 62B and the tip end portion of the second inner cylindrical portion 52B are contacted with each other. Thus, the rear end side gas passage 60A is formed between the rear end outer cylindrical portion 62A and the second inner cylindrical portion 52B. The tip end side gas passage 60B is formed between the tip end outer cylindrical portion 62B and the third inner cylindrical portion 52C, and between the outer bottom portion 63 and the inner bottom portion 53.

In the other gas sensor 1, the detection gas G, flowing into the rear end side gas passage 60A through the outer through hole 621 from outside the outer cover 6, flows inside the inner cover 5 through the inner through hole 521 from the rear end side gas passage 60A. The detection gas G flows into the tip end side gas passage 60B through the inner through hole 521 from inside the inner cover 5. Then, the detection gas G can flow outside the outer cover 6 through the outer through hole 631 from the tip end side gas passage 60B. According to the configuration of the inner cover 5 and the outer cover 6 in the other gas sensor 1, gas flow of the detection gas G in the gas passage 60 can be appropriately controlled.

[Manufacturing Method]

The inner flange portion 51 and the outer flange portion 61 are supported between the insulator 3 and the housing 4.

First, the inner cover 5 is disposed inside the outer cover 6. At this time, the inner cylindrical portion 52 and the outer cylindrical portion 62 are overlapped, and the inner flange portion 51 and the outer flange portion 61 are overlapped. Then, the inner cover 5 and the outer cover 6 are inserted in the small hole portion 411 of the support hole 41 of the housing 4. At this time, the inner flange portion 51 and the outer flange portion 61 are held by the step portion 413 of the housing 4. Note that the inner cover 5 can be disposed inside the outer cover 6 after the outer over 6 is inserted into the support hole 41.

Next, a portion in the tip end side L1 of the insulator 3 is disposed in the inner cylindrical portion 52 of the inner cover 5. Then, talc powder, the sealing member 44 such as sleeve seal are provided in a gap formed between the housing 4 and the insulator 3 in the large hole portion 412 of the support 41 of the housing 4. After that, a portion of the housing 4 in the rear end side L2 in the insertion direction L is bent inward the radial direction R so as to caulk the housing 4 and the insulator 3 via the sealing member 44.

At this time, as shown in FIG. 7, by receiving a bending force that bends the portion of the housing 4 in the rear end side L2 inward the radial direction R, the insulator opposing surface 321 approaches the housing opposing surface 414, the inner flange portion 51 and the outer flange portion 61 are pressed between the insulator opposing surface 321 and the housing opposing surface 414, thereby being supported therebetween. As a result, as shown in FIG. 3, the end portion of the inner flange portion 51 and the end portion of the outer flange portion 61 are strongly pressed by the insulator opposing surface 321 and the housing opposing surface 41, whereby the end portion of the inner flange portion 51 and the outer flange portion 61 are crushed as a plastic-deformation. When the corner portion 613 of the outer flange portion 61 contacts with the surface 512A in the end portion of the inner flange portion 51, the corner portion 613 of the outer flange portion 61 protrudes into the surface 512A of the inner flange portion 51, while the end portion of the inner flange portion 51 is plastically deformed.

[Effects and Advantages]

According to the gas sensor 1, both of the inner flange portion 51 of the inner cover 5 and the outer flange portion 61 of the outer cover 6 are supported between the insulator opposing surface 321 and the housing opposing surface 414. That is, unlike a case where a flange portion supported between the insulator opposing surface 321 and the housing opposing surface 414, is provided at only either the inner cover 5 or the outer cover 6, the inner cover 5 and the outer cover 5 can be reliably prevented from separating from the gas sensor.

Considering a conventional gas sensor in which a flange portion is provided only for either one of the inner cover 5 or the outer cover 6, the other cover is required to be adjoined to either the inner cover 5 or the outer cover 6. The jointing is required to have strong enough strength to fix the other cover among the inner cover 5 and the outer cover 6 to either one cover. Hence, the volume of the joint portion becomes larger.

As a result, considering a case where the conventional gas sensor is exposed to high temperature during the operation, strength of the inner cover 5 and the outer cover 6 is remarkably decreased in the joint portion so that the inner cover 5 and the outer cover 6 may detach from the gas sensor. On the other hand, a joint portion having large volume is not required for the gas sensor 1 in which both of the inner flange portion 51 of the inner cover 5 and the outer flange portion 61 of the outer cover 61 are supported between the insulator opposing surface 321 and the housing opposing surface 414. Hence, the inner cover 5 or the outer cover 6 can be prevented from separating from the gas sensor during the operation thereof.

It is preferable that the joint portion is not formed using a welding or the like between the inner cylindrical portion 52 of the inner cover 5 and the outer cylindrical portion 62 of the outer cover 62. However, a joint portion having smaller volume may be formed, by welding or the like, between the inner cylindrical portion 52 of the inner cover 5 and the outer cylindrical portion 62 of the outer cover 6, in order to keep the positional relationship therebetween. An allowable volume of the joint portion to be formed can be determined within a range such that degree of a decrease in the strength during the heating does not cause separation of the inner cover 5 and the outer cover 6.

According to the gas sensor 1 of the present embodiment, the end face 511 of the inner flange portion 51 is positioned closer to the outer side R1 in the radial direction R than the end face 611 of the outer flange portion 61, and the corner portion 613 of the outer flange portion 61 protrudes the surface 512A of the inner flange portion 51. Thus, the air tightness between the insulator opposing surface 321 and the housing opposing surface 414 can be maintained at high level so that detection accuracy of the gas can be maintained at high level.

In the case where the air tightness is not maintained between the inner flange portion 51 and the outer flange portion 61, the detection gas G flowing into the gap between the inner cover 5 and the outer cover 6 may enter deep inside the support hole 41 of the housing 4 through the gap between the inner flange portion 51 and the outer flange portion 61. According to the gas sensor 1 of the present embodiment, the detection gas G is introduced into the detecting portion 21 positioned in the tip end side L1 of sensor element 2 in the insertion direction L, and the reference gas A in introduced into the duct 24 from the rear end portion of the sensor element 2 in the insertion direction L.

The detection portion 21 of the sensor element 2 utilizes a difference between the oxygen concentration in the reference gas A and the oxygen concentration in the detection gas G to perform gas detection. Therefore, if the detection gas G is mixed with the reference gas A which is reference for the gas detection, the accuracy of the gas detection is deteriorated. Accordingly, in this respect, it is important to prevent the detection gas G from flowing into the rear end side L2 of the support hole 41 of the housing 4, from among a gap between the insulator opposing surface 321 and the inner flange portion 51, or a gap between the outer flange portion 61 and the housing opposing 414, or a gap between the inner flange portion 51 and the outer flange portion 61. Specifically, because of the following reason, it is important to secure the air tightness between the inner flange portion 51 and the outer flange portion 61.

As shown in FIG. 3, in the case where the inner flange portion 51 and the outer flange portion 61 are supported between the insulator opposing surface 321 and the housing opposing surface 414, boundary portions K1, K2 and K3 are formed, where the members 3, 4, 51 and 61 are contacted, at respective gaps including the gap between the insulator opposing surface 321 and the inner flange portion 51, the gap between the housing opposing 414 and the outer flange portion 61, and the gap between the inner flange portion 51 and the outer flange portion 61. In the boundary portions K1, K2 and K3 after assembling the gas sensor 1, the members 3, 4, 51 and 61 are contacted with each other due to the caulking force of the housing 4. However, when using the gas sensor 1, the gas sensor 1 is heated by the heater 25 and the exhausted gas as the detection gas G. At this time, there is a concern that a gap may be formed in a portion among the boundary portions K1, K2 and K3, because of thermal stress or the like occurred between the members 3, 4, 51, and 61.

As shown in FIG. 3, the following state is formed in the boundary portion K1 between the insulator opposing surface 321 and the surface 512B of the inner flange portion 51. The insulator 3 is made of a ceramic material and the inner cover 5 is made of metal. The surface roughness of the insulator 3 is larger than that of the inner cover 5, and the rigidity of the insulator 3 is larger than that of the inner cover 5. Hence, in the assembling process of the gas sensor 1, when the inner flange portion 51 and the outer flange portion 61 are supported between the insulator opposing surface 321 and the housing opposing surface 414, the surface 512B of the inner flange portion 51 is considered to be plastically deformed along fine roughness of the insulator opposing surface 321 when viewing microscopically the boundary portion K1 between the insulator opposing surface 321 and the surface 512B of the inner flange portion 51. As a result, a surface area of a portion where both sides are contacted with each other, is increased in the boundary portion K1 between the insulator opposing surface 321 and the surface 512B of the inner flange portion 51, thereby increasing a frictional force that influences the boundary portion K1 between the insulator opposing surface 321 and the surface 521B of the inner flange portion 512B.

Then, in the case where the gas sensor 1 is heated at high temperature, since the coefficient of linear expansion of the inner flange portion 51 is higher than that of the insulator 3, the inner flange portion 51 expands and tends to separate from the insulator opposing surface 321. At this time, a large frictional force influences the boundary portion K1 between the insulator opposing surface 321 and the surface 512B of the inner flange portion 51, whereby the inner flange portion 51 is unlikely to expand in a direction where the inner flange portion 51 tends to separate. Therefore, a gap is unlikely to be produced at the boundary portion K1 formed between the insulator opposing surface 321 and the surface 512B of the inner flange portion 51.

As shown in FIG. 3, the following state is formed in the boundary portion K2 between the housing opposing surface 414 and the surface 612A of the outer flange portion 6. Each of the housing 4 and the outer cover 6 is made of metal.

There is no significant difference between the coefficients of linear expansion of the housing 4 and the outer cover 6. Also, there is no significant difference between the surface roughness of the housing 4 and the surface roughness of the outer cover 6. Accordingly, when the gas sensor 1 is heated at high temperature, the thermal expansion of the housing 4 and the outer flange portion 61 are approximately the same. As a result, when the gas sensor 1 is used, a gap is unlikely to be formed in the boundary portion K2 formed between the housing opposing surface 414 and the outer flange portion 61.

As shown in FIG. 3, the following state is formed in the boundary portion K3 between the surface 512A of the inner flange portion 51 and the surface 612B of the outer flange portion. Each of the inner flange portion 51 and the outer flange portion 61 is made of metal. There is no significant difference between the coefficients of linear expansion of the inner flange portion 51 and the outer flange portion 61. Also, there is no significant difference between the surface roughness of the inner flange portion 51 and the surface roughness of the the outer flange portion 61. Hence, when the gas sensor 1 is heated at high temperature, the coefficients of linear expansion of the inner flange portion 51 and the outer flange portion 61 are approximately the same. At this time, the inner flange portion 51 is influenced by the large frictional force at the boundary portion K1 between the insulator opposing surface 321 and the surface 512B of the inner flange portion 51, whereby the inner flange portion 51 is unlikely to expand in a direction where the inner flange portion 51 tends to separate. On the other hand, the outer flange portion 61 expands together with the housing 4. As a result, when the gas sensor 1 is used, a gap is likely to be produced at the boundary portion K3 between the surface 512A of the inner flange portion 51 and the surface 612B of the outer flange portion 51.

According to the gas senor 1 of the present embodiment, the structure of the boundary portion K3 where a gap is likely to be formed is appropriately considered to produce a state where the corner portion 613 of the outer flange portion 61 protrudes the surface 512A of the inner flange portion 51. Thus, in the case where the gas sensor is used and a gap is being produced between the surface 512A of the inner flange portion 51 and the surface 612B of the outer flange portion 61, frictional force due to the intrusion is produced between the corner portion 613 and the surface 512A. Therefore, a positional offset is unlikely to be produced at the boundary portion K3 formed between the surface 512A of the inner flange portion 51 and the surface 612B of the outer flange portion 61. Hence, a gap is not produced at the boundary portion K3.

Note that the effects of avoiding the gap formed in the boundary portion K3 can be obtained similarly for a case where the end portion of the inner flange portion 51 is bent overhanging the corner portion 61.

Thus, according to the gas sensor 1 of the present embodiment, when using the gas sensor 1, gaps are not produced at the boundary portions K1, K2 and K3 as described above. Thus, the detection gas G is prevented from being mixed with the reference gas A which is introduced in the sensor element 2 so that the detection accuracy of the gas to be detected by the detection portion 21 of the sensor element 2 can be maintained at high level.

Figure 12:
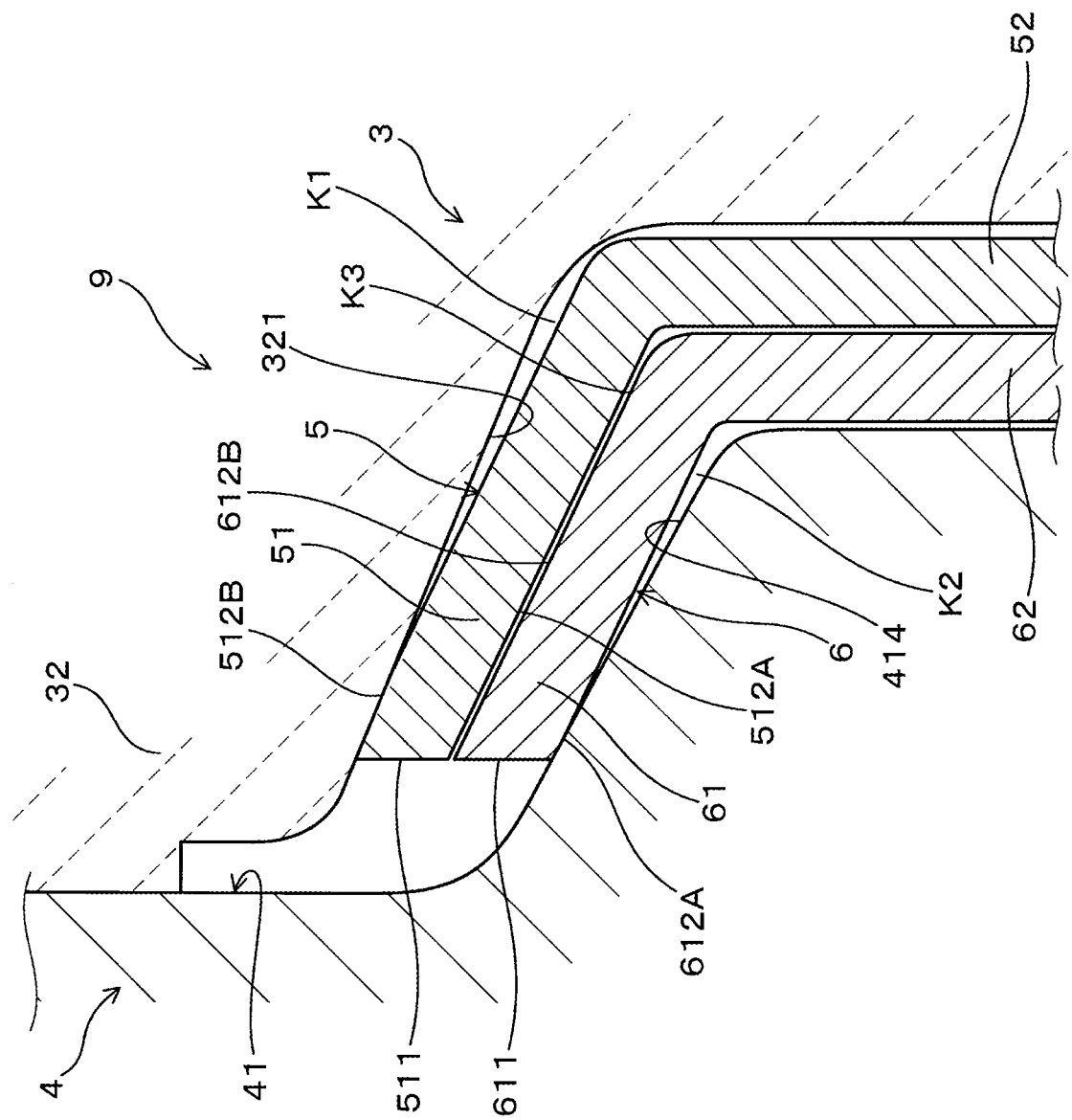
FIG. 12 is a cross-sectional view showing an inner flange portion and an outer flange portion supported between the insulator and the housing according to a comparative embodiment, as being enlarged in the peripheral portion thereof.

FIG. 12 shows a gas sensor 9 according to a comparative embodiment in which the position of the end face 511 of the inner flange portion 51 and the position of the end face 611 of the outer flange portion 61 are flush with each other. Likewise, in the gas sensor 9, gaps are unlikely to be formed in the boundary portion K1 formed between the insulator opposing surface 321 and the surface 512B of the inner flange portion 51, and the boundary portion K2 formed between the housing opposing surface 414 and the surface 612A of the outer flange portion 61 K2.

On the other hand, when the gas sensor 9 is heated, a positional offset is likely to be produced at the boundary portion K3 between the surface 512A of the inner flange portion 51 and the surface 612B of the outer flange portion 61. There is no significant difference between the coefficients of linear expansion of the inner flange portion 51 and the outer flange portion 61. Also, there is no significant difference between the surface roughness of the inner flange portion 51 and the surface roughness of the outer flange portion 61. Hence, when the gas sensor 9 is heated, a positional offset is produced between the surface 512A of the inner flange portion 51 and the surface 612B of the outer flange portion 61 so that a gap may be formed at the boundary portion K3. Hence, according to the gas sensor 1 of the present embodiment, where the corner portion 613 of the outer flange portion 61 protrudes the surface 512A of the inner flange portion 51, an effect of avoiding production of gaps between the surface 512A of the inner flange portion 51 and the surface 612B of the outer flange portion 61 can be obtained.

Accordingly, the gas sensor 1 of the present embodiment can prevent the inner cover 5 or the cover 6 from falling off the gas sensor 1 when being used, and the air tightness between the insulator 3 and the housing 4 is maintained at high level so that high detection accuracy of the gas detection can be obtained.

(Second Embodiment)

The present embodiment will be described only for a case where an alignment of the positional offset between the end face 511 of the inner flange portion 51 and the end face 611 of the outer flange portion 61 is different from that of the first embodiment.

Figure 13:
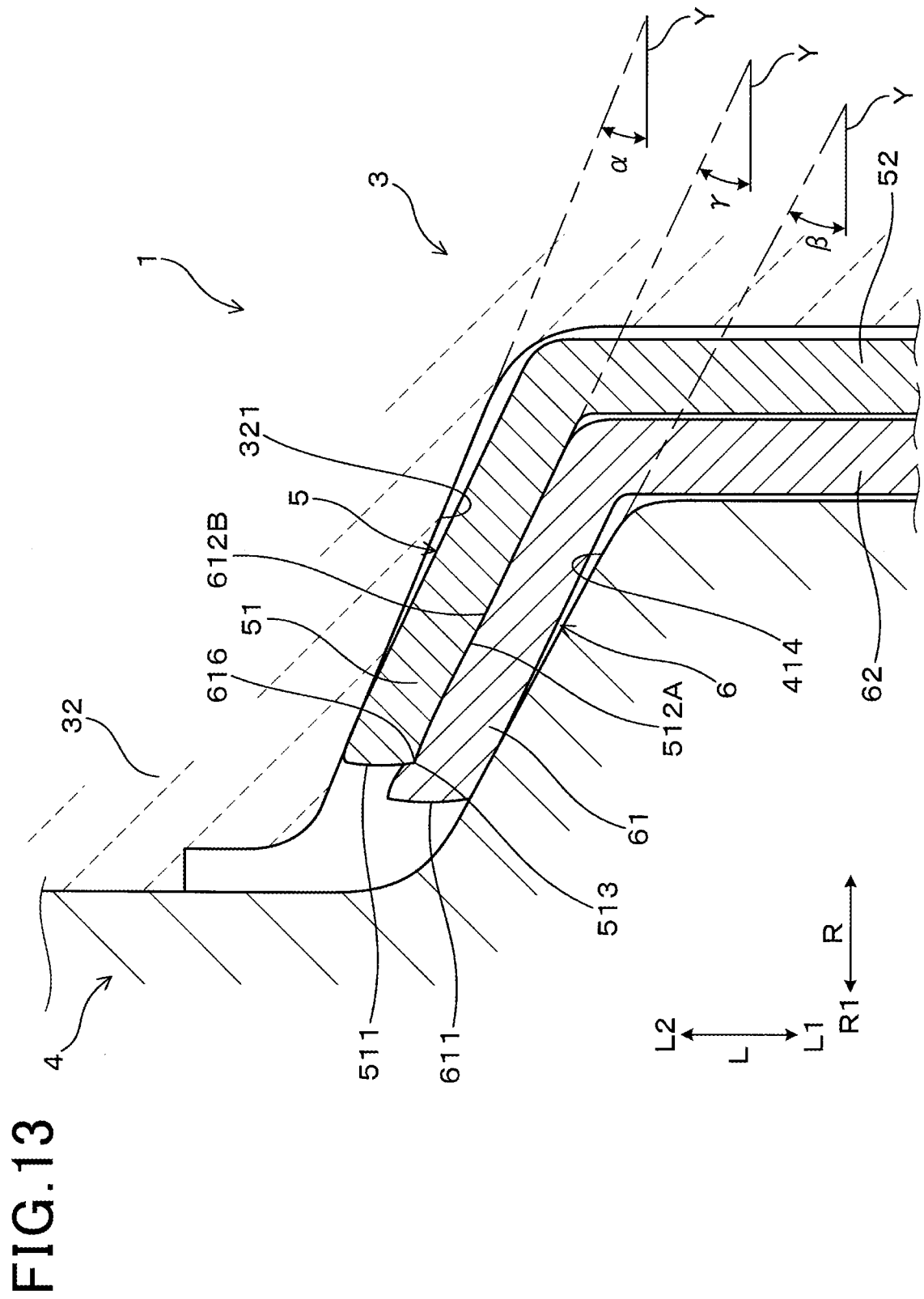
FIG. 13 is a cross-sectional view showing an inner flange portion and an outer flange portion supported between the insulator and the housing according to a second embodiment, as being enlarged in the peripheral portion thereof.

According to the gas sensor 1 of the present embodiment, as shown in FIG. 13, the end face 611 of the entire periphery of the outer flange portion 61 in the circumferential direction C is positioned in the outer side R1 in the radial direction R than the end face 511 of the entire periphery of the inner flange portion 51 in the circumferential direction C. Also, the corner portion 513 in the inner flange portion 51, formed between the end face 511 and the surface 512A in the tip end side L1 in the insertion direction L, protrudes into the surface 612b in the rear end side L2 in the insertion direction L. A depression part 516 caused by the intrusion of the corner portion 513 is formed on the surface 612A of the outer flange portion 61.

Figure 14:
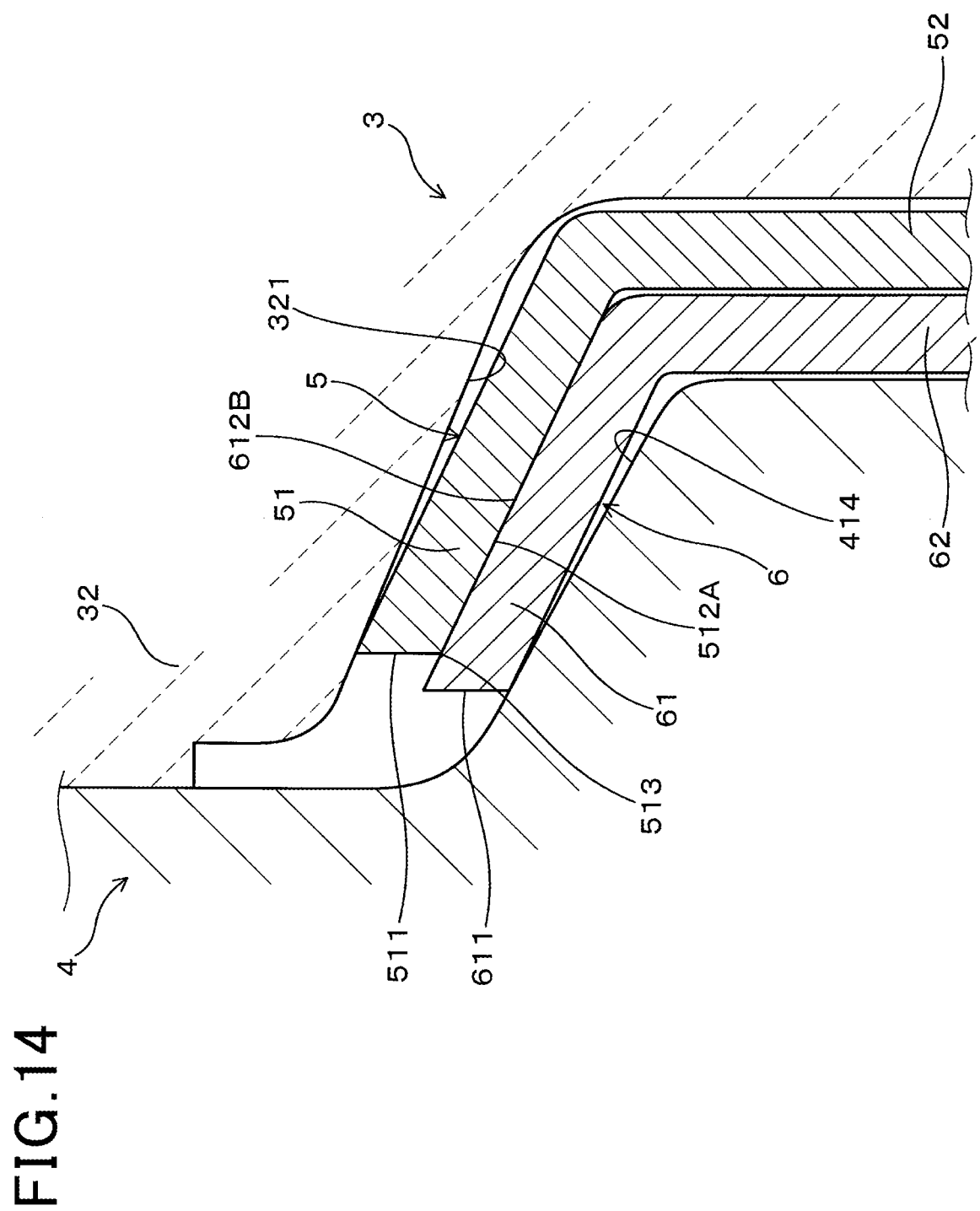
FIG. 14 is a cross-sectional view showing an inner flange portion and an outer flange portion before being supported between the insulator and the housing according to the second embodiment, as being enlarged in the peripheral portion thereof.

As shown in FIG. 14, in an initial state of the inner cover 5 and the outer cover 6 before assembling the gas sensor 1 of the present embodiment, the end face 511 of the inner flange portion 51 is formed in approximately parallel to the insertion direction L, and also the end face 611 of the outer flange portion 61 is formed in approximately parallel to the insertion direction L. In the initial state, the corner portion 513 of the inner flange portion 51, formed between the end face 511 and the surface 512A in the tip end side L1, is formed in an obtuse angle shape. Note that the shape of the angle portion 513 is kept in the obtuse angle shape even after assembling the gas sensor 1.

After disposing the inner flange portion 51 and the outer flange portion 61 between the insulator opposing surface 321 and the housing opposing surface 414, the end portions of the inner flange portion and the outer flange portion 61 are plastically deformed. Then, each of the end face 511 of the inner flange portion 51 and the end face 611 of the outer flange portion 61 after assembling the gas sensor 1, may be inclined with respect to the insertion direction L or may be bent in a curved shape.

Figure 15:
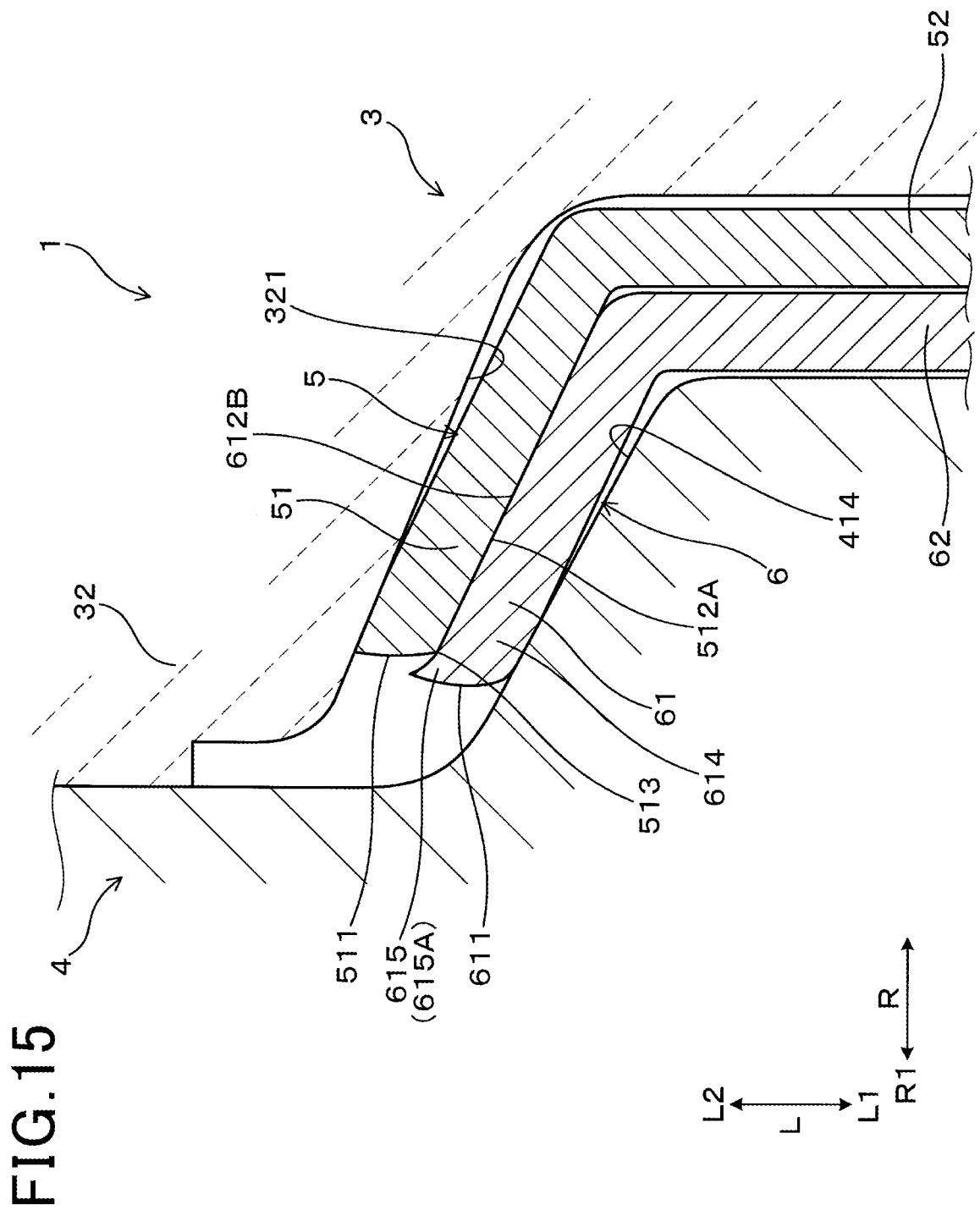
FIG. 15 is a cross-sectional view showing other inner flange portion and outer flange portion supported between the insulator and the housing according to the second embodiment, as being enlarged in the peripheral portion thereof.

The engagement between the inner flange portion 51 and the outer flange portion 61 can be as follows. That is, instead of a case where the corner portion 513 of the inner flange portion 51 protrudes into the surface 612B, as shown in FIG. 15, the end portion in the outer flange portion 61 may be bent overhanging the corner portion 513 between the end face 511 and the surface 512A of the inner flange portion 51 in the tip end side L1 in the insertion direction. In this case, a bend portion 615A is formed in the end portion 615 of the outer flange portion 61. The bend portion 615A is bent with respect to a body 614 connected to the outer cylindrical portion 62 of the outer flange portion 61. In this case, a portion around the bending point of the bend portion 615A in the rear end side L2 of the outer flange portion 61 contacts with the corner portion 513 of the inner flange portion 51.

According to the present embodiment, a relationship between the inclination angle α of the insulator opposing surface 321, the inclination angle β of the housing opposing surface 414 and the inclination angle γ of the inner flange portion 51 and the outer flange portion 61 are similar to that of the first embodiment. Moreover, other configurations of the gas sensor 1, effects and advantages or the like are the same as that of the first embodiment. According to the present embodiment, elements having the same reference signs as the first embodiment are the same as the corresponding element of the first embodiment.

(Third Embodiment)

The present embodiment differs from the first embodiment in that the relationship between the inclination angle α of the insulator opposing surface 321, the inclination angle β of the housing opposing surface 414 and the inclination angle γ of the inner flange portion 51 and the outer flange portion 61.

Figure 16:
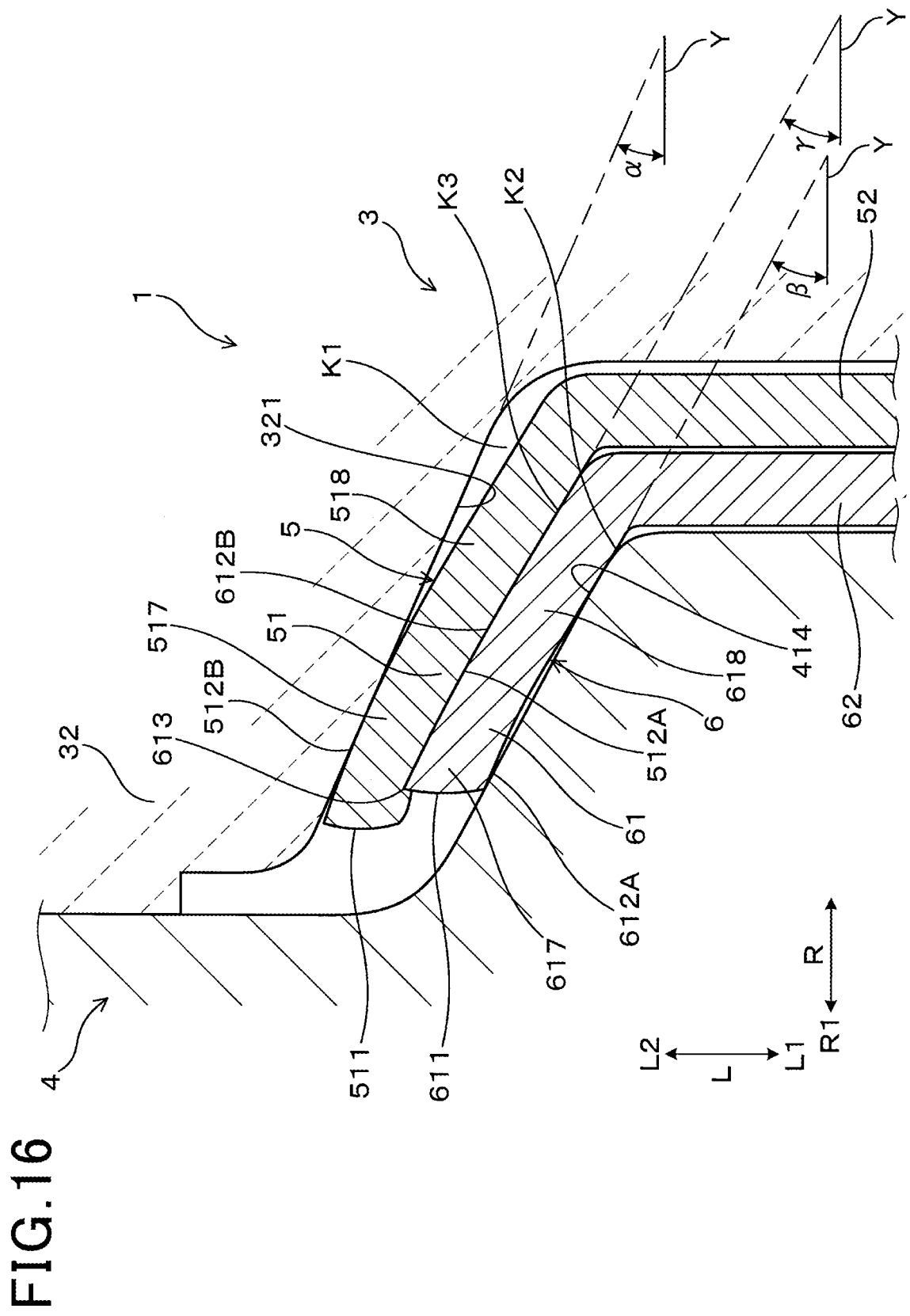
FIG. 16 is a cross-sectional view showing an inner flange portion and an outer flange portion supported between the insulator and the housing according to a third embodiment, as being enlarged in the peripheral portion thereof.

As shown in FIG. 16, the end face 511 of the inner flange portion 51 of the present embodiment is positioned in the outer side R1 in the radial direction R than the end face 611 of the outer flange portion 61. The corner portion 613 formed between the end face 611 and the surface 612B in the outer flange portion 61 protrudes into the surface 512A of the inner flange portion 51.

According to the present embodiment, the inclination angle γ of the inner flange portion and the outer flange portion 61 is larger than the inclination angle β of the housing opposing surface 414, and the inclination angle β of the housing opposing surface 414 is larger than the inclination angle α of the insulator opposing surface 321. In other words, according to the gas sensor 1 of the present embodiment, a relationship α<β<γ is satisfied. The difference between the inclination angle α of the insulator opposing surface 321 and the inclination angle γ can be set within a range from 0.5° to 10°. When these inclination angles α and β are small, effects of intrusion into the surface 512A is unlikely to obtain. On the other hand, when the difference between the inclination angles α and β is too large, a contact area among the insulator 3, the inner flange portion 51, the outer flange portion 61 and the housing 4 becomes small. Each of the inclination angles α, β, γ is expressed as an angle relative to a virtual reference line Y which is parallel to the radial direction R. The inclination angles of the insulator opposing surface 321, the housing opposing surface 414, and the inner flange portion 51 and the outer flange portion 61 are the same as that of the first embodiment.

Figure 17:
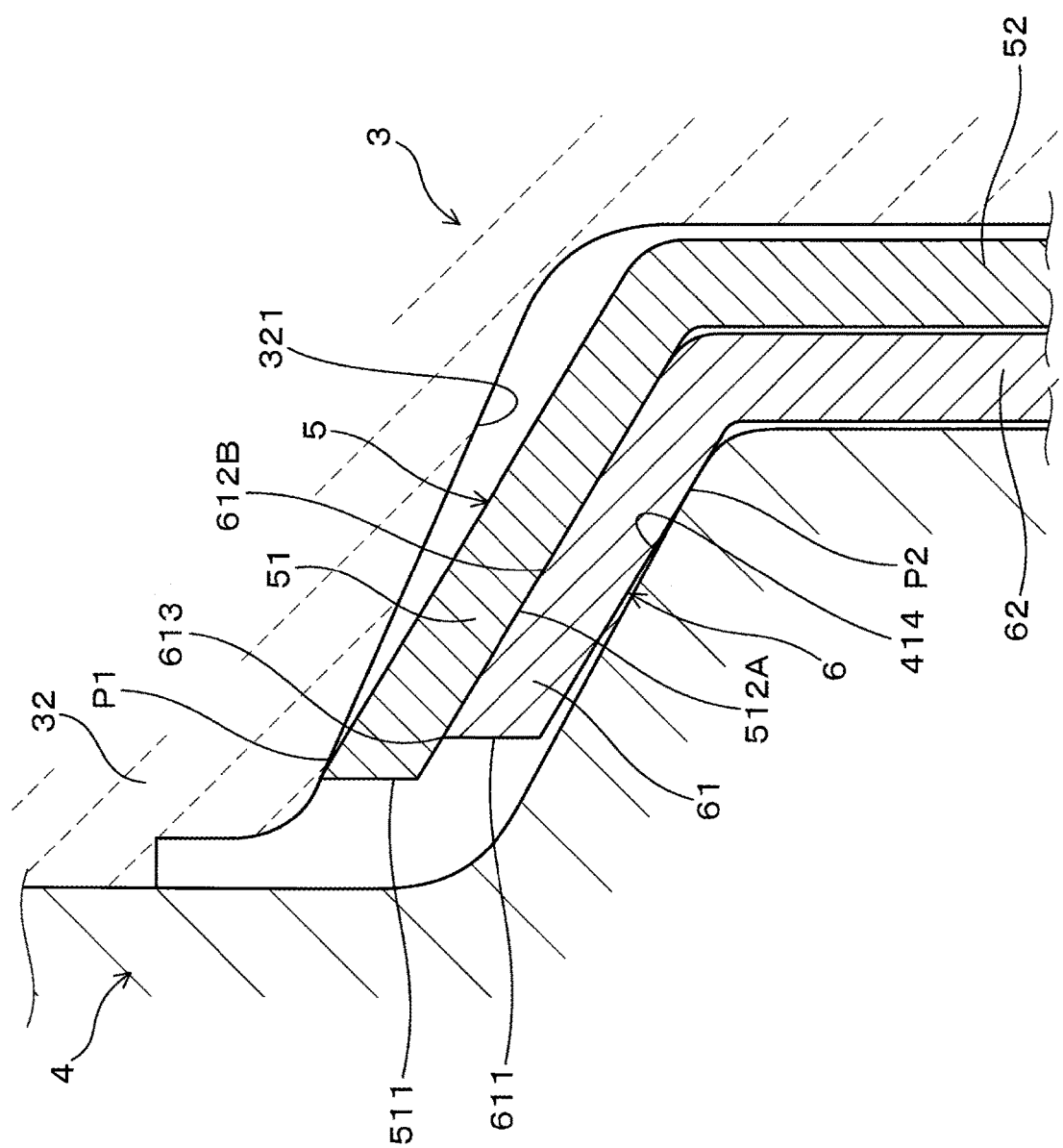
FIG. 17 is a cross-sectional view showing an inner flange portion and an outer flange portion before being supported between the insulator and the housing according to the third embodiment, as being enlarged in the peripheral portion thereof.

According to this configuration in the present embodiment, the outer periphery side portion 517 of the surface 512B in the rear end side L2 of the inner flange portion 51 is likely to contact with the insulator opposing surface 321, and the inner periphery side portion 618 of the surface 612A in the tip end side L1 of the outer flange portion 61 is likely to contact with the housing opposing surface 414. As shown in FIG. 17, a portion P1 around the tip end portion of the surface 512B of the inner flange portion 51 strongly contacts with the insulator opposing surface 321, whereby the boundary portion K1 between the insulator opposing surface 321 and the surface 512B of the inner flange portion 51 is securely occluded. Also, the inner periphery portion P2 of the surface 612A of the outer flange portion 61 strongly contacts with the housing opposing surface 414, whereby the boundary portion K2 between the housing opposing surface 414 and the surface 612A of the outer flange portion 61 is securely occluded.

As shown in FIGS. 16 and 17, in the case where the inner flange portion 51 and the outer flange portion 61 of the present embodiment is disposed between the insulator opposing surface 321 and the housing opposing surface 414, the outer periphery side portion 517 of the inner flange portion 51 is strongly pressed by the insulator opposing surface 321. Then, the outer periphery side portion 517 of the inner flange portion 51 is elastically deformed to be bent towards the tip end side L1 in the insertion direction L with respect to the inner periphery side portion 518 of the inner flange portion 51. The outer periphery side portion 617 of the outer flange portion 61 is elastically deformed to be bent towards the tip end side L1 in the insertion direction L with respect to the inner periphery side portion 618 of the outer flange portion 61. In some cases, the outer periphery side portion 517 of the inner flange portion 51 and the outer periphery side portion 617 of the outer flange portion 61 are plastically deformed to be bent towards the tip end side L1 in the insertion direction L.

FIG. 17 illustrates a state before disposing the inner flange portion 51 and the outer flange portion 61 between the insulator opposing surface 321 and the housing opposing 414. Note that the inclination angles between the inclination angles α, β, γ are exaggerated in FIG. 7 since the difference therebetween is small. An amount of elastic-deformation of the inner flange portion 51 and the outer flange portion 61 is small.

According to the gas sensor 1 of the present embodiment, the insulator opposing surface 321 and the housing opposing surface 414 cause the plastic-deformation of the inner flange portion 51 and the outer flange portion 61, whereby spring force that dissolves the elastic-deformation effects the inner flange portion 51 and the outer flange portion 61. With this spring force, the boundary portion K1 between the insulator opposing surface 321 and the surface 512B of the inner flange portion 51, the boundary portion K2 between the housing opposing surface 414 and the surface 612A of the outer flange portion 61, and the boundary portion K3 between the surface 512A of the inner flange portion 51 and the surface 612B of the outer flange portion 61 are occluded. Hence, when the gas sensor 1 is heated, although gaps tend to be formed in each of the boundary portions K1, K2 and K2, spring force affects the inner flange portion 51 and the outer flange portion 61 not to produce the gaps. Thus, the air tightness between the insulator 3 and the housing 4 is maintained at high level so that high detection accuracy of the gas can be maintained.

According to the present embodiment, either the end face 511 of the inner flange portion 51 or the end face 611 of the outer flange portion may be disposed in the outer side R1 of the radial direction R. As described in the second embodiment, the corner portion 513 of the inner flange portion 51 between the end face 511 and the surface 512A in the tip end side L1 in the insertion direction L, may protrude into the surface 612B of the outer flange portion 61 in the rear end portion side L2 in the insertion direction L. Further, either one of the inner flange portion 51 or the outer flange portion 61 may include the bend portions 515A and 616A that bend towards the other side end faces 511 or 611.

Other configurations, effects and advantages in the gas sensor according to the present embodiment, are the similar to that of the present embodiment. Likewise, in the present embodiment, elements having the same reference symbols as that of the first embodiment are equivalent to that of the first embodiment.

(Fourth Embodiment)

Figure 18:
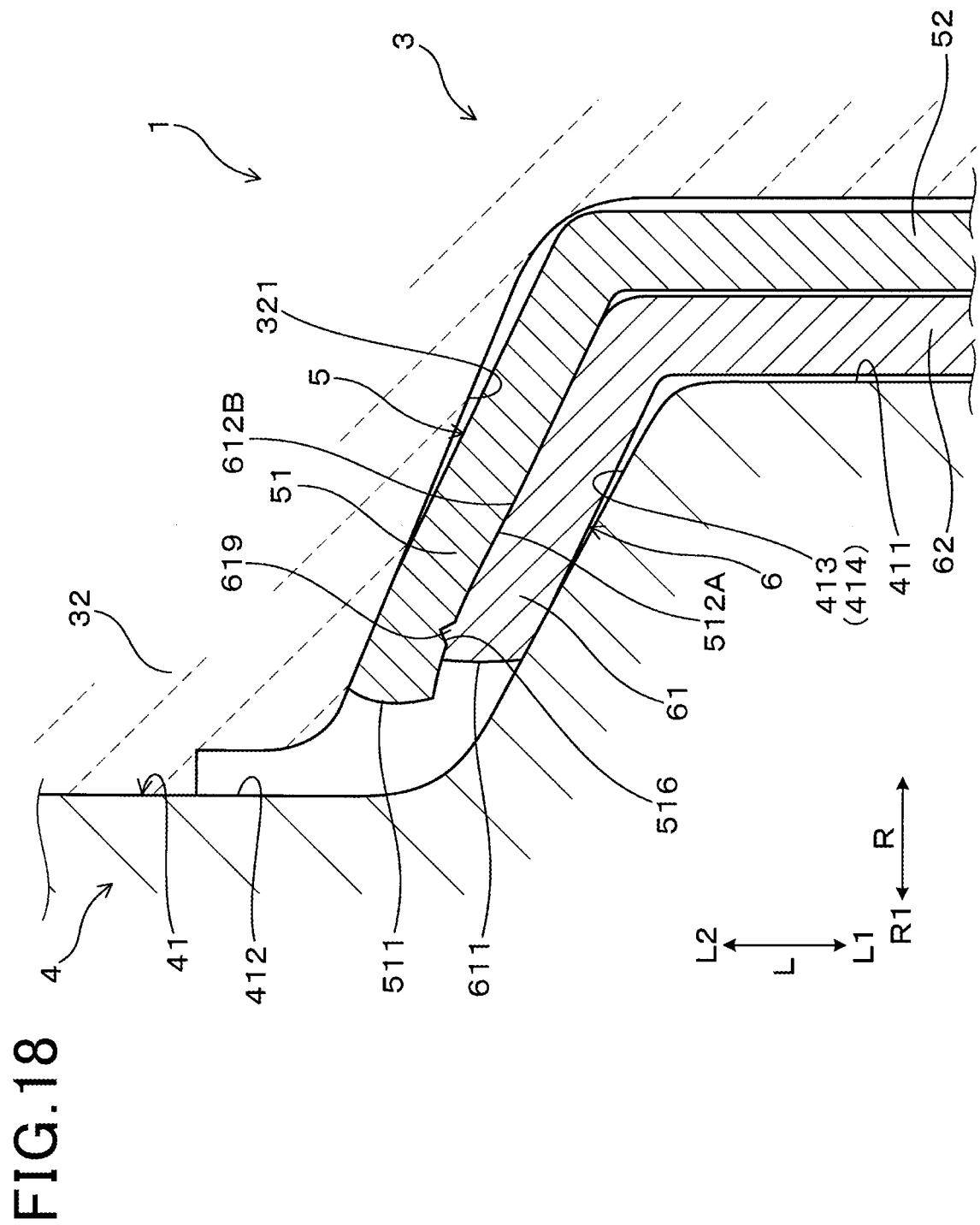
FIG. 18 is a cross-sectional view showing an inner flange portion and an outer flange portion supported between the insulator and the housing according to a fourth embodiment, as being enlarged in the peripheral portion thereof.
Figure 19:
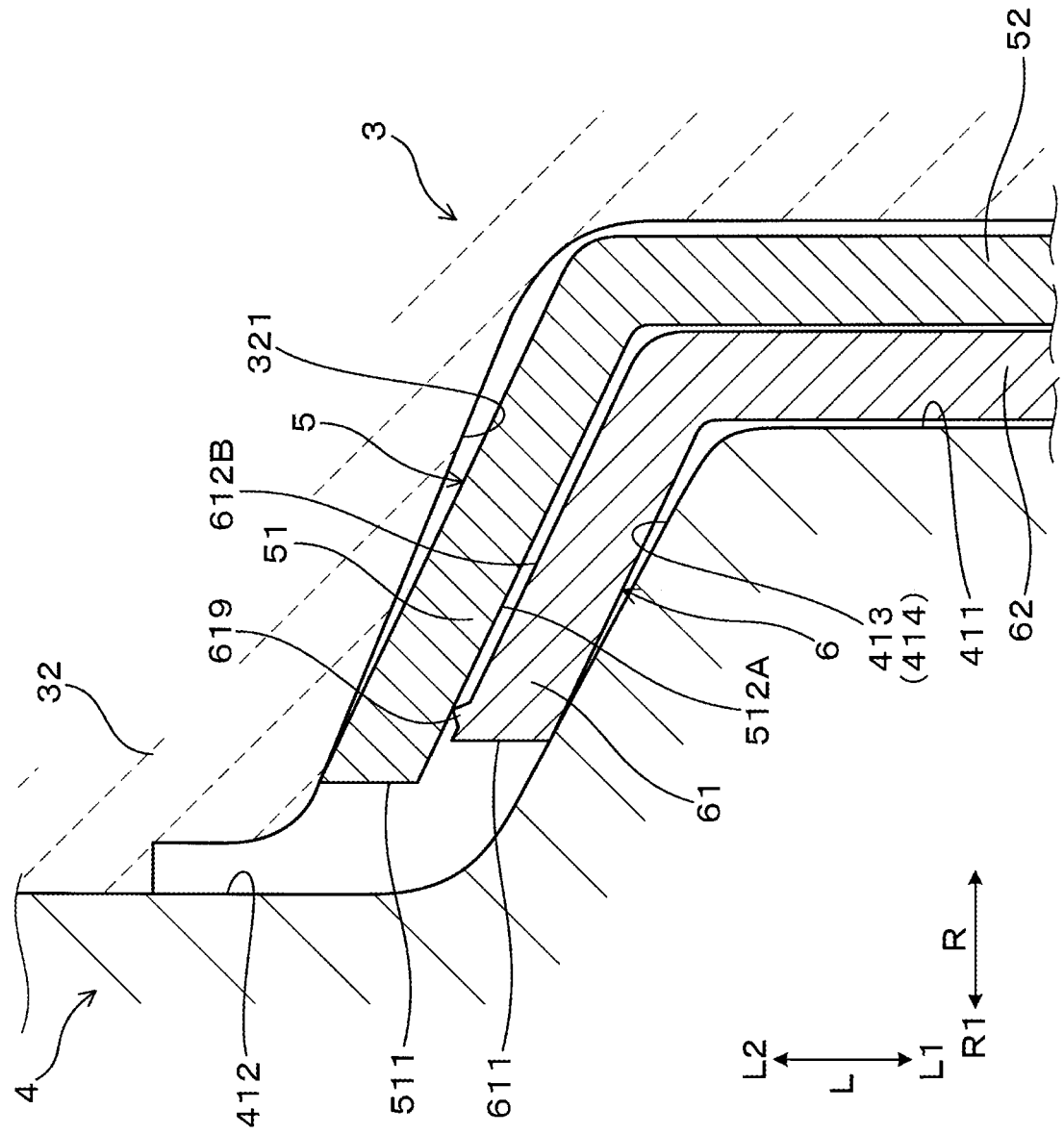
FIG. 19 is a cross-sectional view showing an inner flange portion and an outer flange portion before being supported between the insulator and the housing according to the fourth embodiment, as being enlarged in the peripheral portion thereof.

According to the present embodiment, a case will be described in which a protrusion 619 is provided for intruding the inner flange portion 51 into the surface 512A. FIG. 18 illustrates a state where the protrusion 619 protrudes into the surface 512A of the inner flange portion 619. FIG. 19 illustrates a state before the protrusion 619 protrudes into the surface 512A of the inner flange portion 51. The protrusion 619 is formed by deforming the surface 612B of the outer flange portion 61 is deformed, when forming the outer cover 6. According to the protrusion 619 of the present embodiment, one protrusion is formed over the entire periphery of the outer flange portion 61 in the circumferential direction C. However, a plurality of protrusions 619 can be formed to be arranged in the radial direction R of the outer flange portion 61. The protrusion 619 is formed to have a sharp shape at the tip end in order to readily protrude into the surface 512A of the inner flange portion 51.

Figure 20:
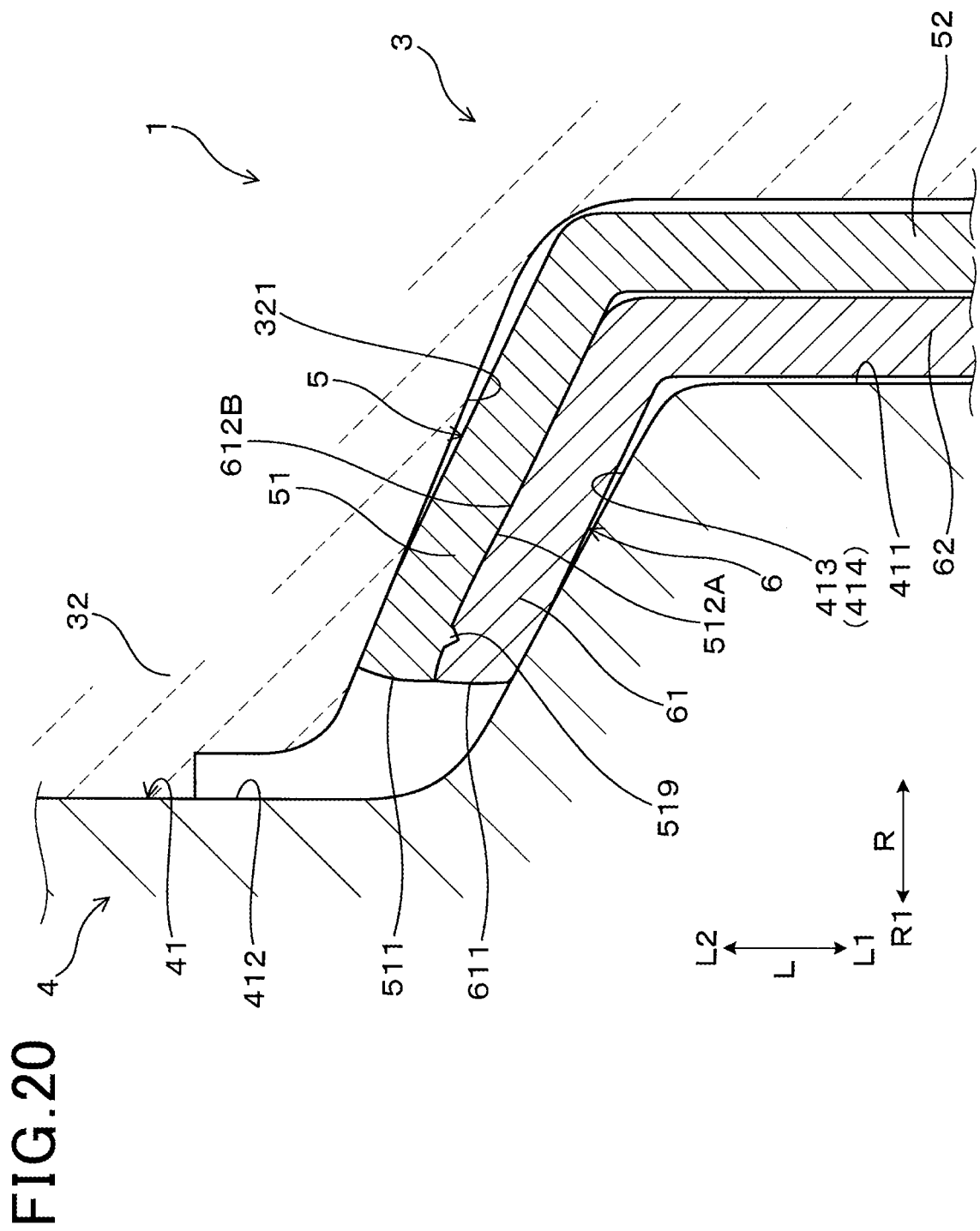
FIG. 20 is a cross-sectional view showing other inner flange portion and outer flange portion supported between the insulator and the housing according to the fourth embodiment, as being enlarged in the peripheral portion thereof.

According to the present embodiment, to utilize the protrusion 619 formed on the surface 612B of the outer flange portion 61, it is not necessary to offset the end face 511 of the inner flange portion 51 and the end face 611 of the outer flange portion 61. According to the present embodiment, the end face 511 of the inner flange portion 51 is positioned in the outer side R1 of the radial direction R than the end face 611 of the outer flange portion 61. Other than this, the end face 611 of the outer flange portion 61 may be positioned radially (with respect to the radial direction R) towards the outer side R1 than the position of the end face 511 of the inner flange portion 51, or the end face 511 of the inner flange portion 51 and the end face 611 of the outer flange portion 61 may be uniform. Also, as shown in FIG. 20, the protrusion 519 may be provided on the surface 512A of the inner flange portion 51 so as to protrude into the surface 612B of the outer flange portion 61.

Other configurations, effects and advantages in the gas sensor according to the present embodiment, are the similar to that of the present embodiment. Likewise, in the present embodiment, elements having the same reference symbols as that of the first embodiment are equivalent to those of the first embodiment.

(Fifth Embodiment)

Figure 21:
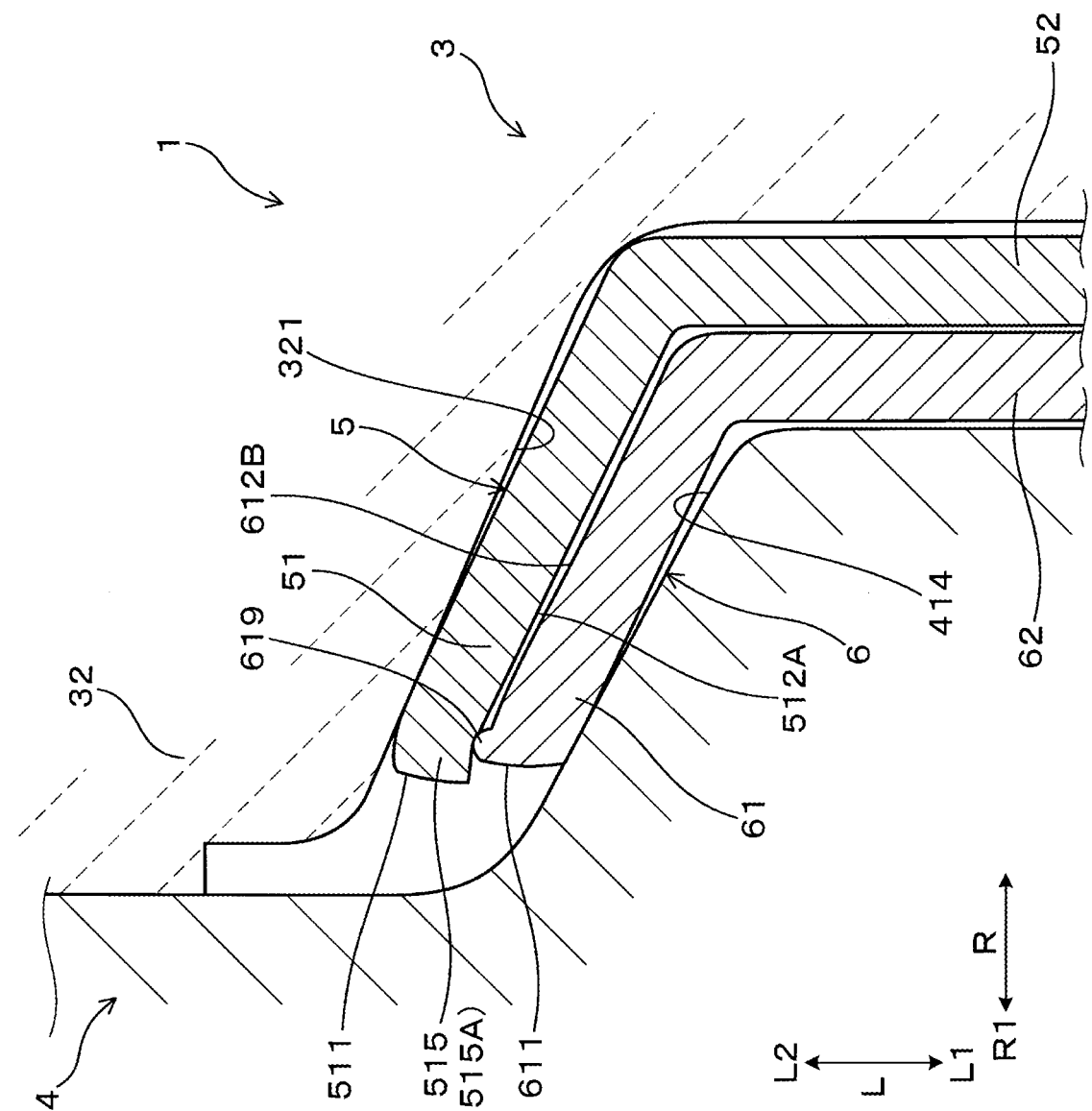
FIG. 21 is a cross-sectional view showing an inner flange portion and an outer flange portion supported between the insulator and the housing according to a fifth embodiment, as being enlarged in the peripheral portion thereof.
Figure 22:
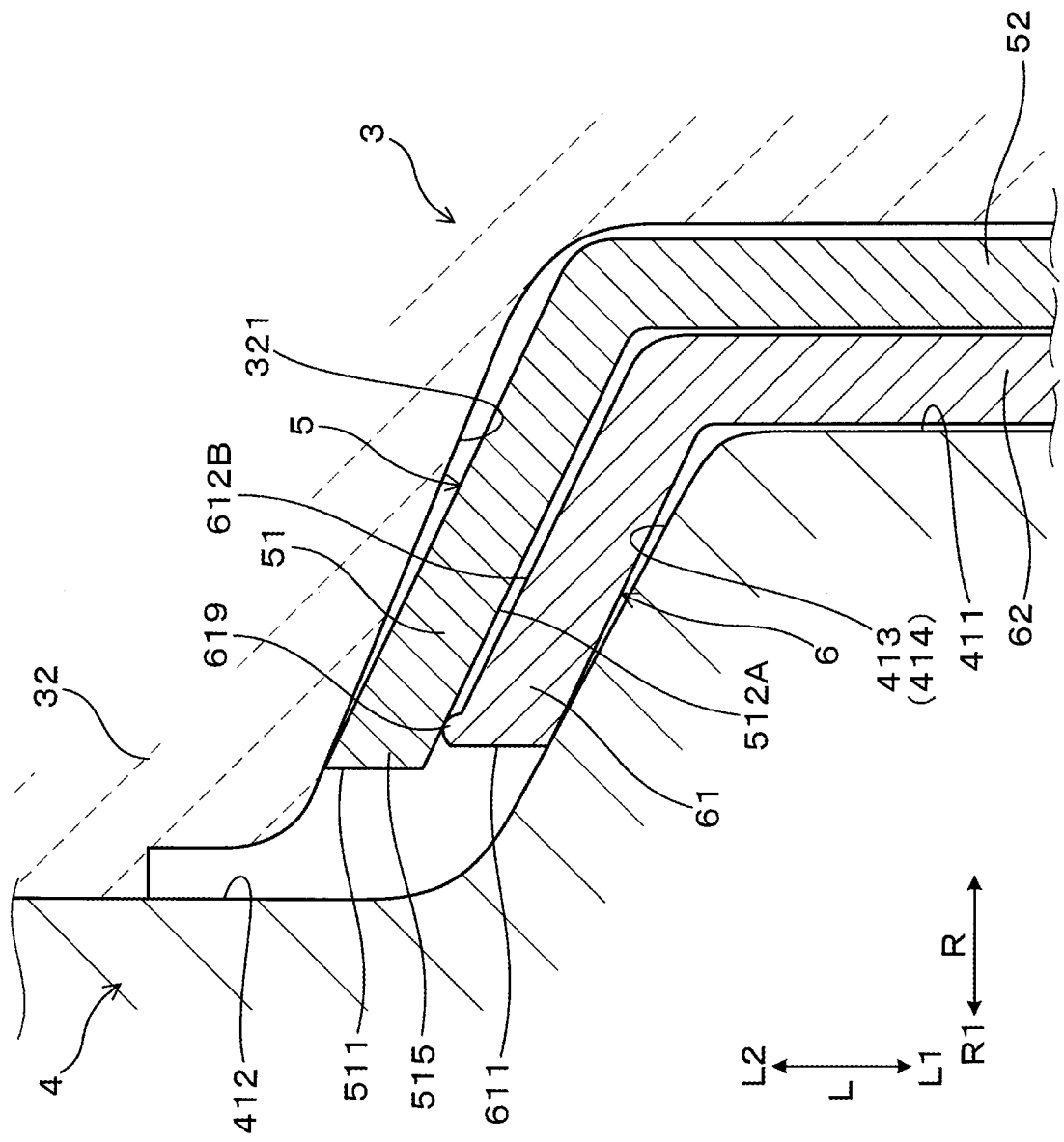
FIG. 22 is a cross-sectional view showing an inner flange portion and an outer flange portion before being supported between the insulator and the housing according to the fifth embodiment, as being enlarged in the peripheral portion thereof.

According to the present embodiment, a case will be described in which a protrusion 619 is provided to bend the end face 515 of the inner flange portion 51. FIG. 21 illustrates a state where the end face 515 is bent by the protrusion 619, and overhanging the protrusion 619. FIG. 22 illustrates a state before the end portion 515 of the inner flange portion 51 is bent by the protrusion 619. The protrusion 619 is formed by deforming the surface 612B of the outer flange portion 61, when the outer cover 6 is formed.

The protrusion 619 of the present embodiment is formed as one protrusion over the entire periphery of the outer flange portion 61 in the circumferential direction C. However, a plurality of protrusions 619 can be formed to be arranged in the radial direction R of the outer flange portion 61. The protrusion 619 of the present embodiment is formed to have an arc shape at the tip end for easily bending the end portion 515 of the inner flange portion 51.

Figure 23:
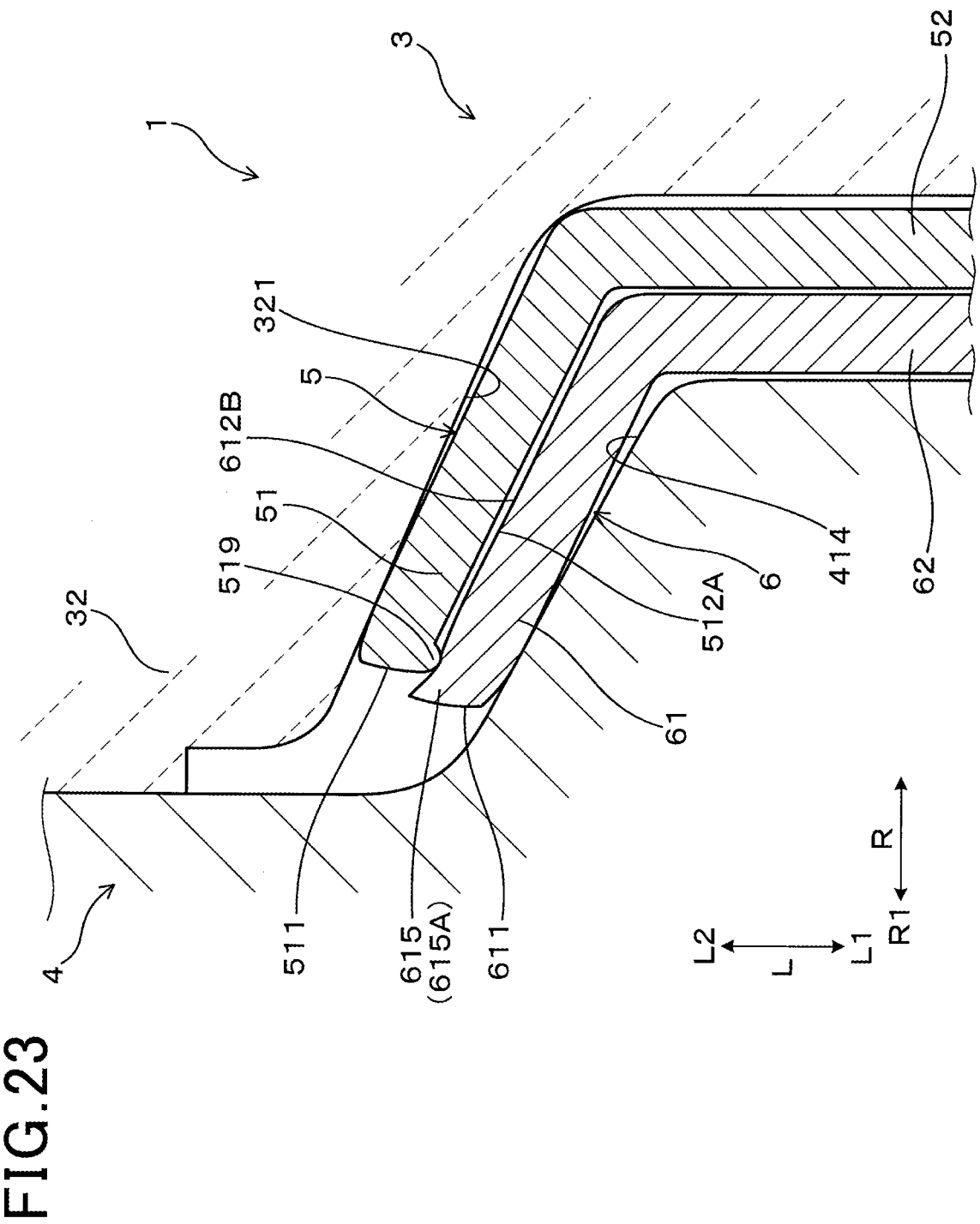
FIG. 23 is a cross-sectional view showing other inner flange portion and outer flange portion supported between the insulator and the housing according to the fifth embodiment, as being enlarged in the peripheral portion thereof.

According to the present embodiment, the end face 511 of the inner flange portion 51 is positioned in the outer side R1 of the radial direction R than the end face 611 of the outer flange portion 61 by utilizing the protrusion 619 formed on the surface 612B of the outer flange portion 61 to bend the end portion 515 of the inner flange portion 51. Also, the protrusion 619 is formed at the tip end portion of the surface 612B of the outer flange portion 61 so as to bend the end portion 515 of the inner flange portion 51 easily. Further, as shown in FIG. 23, the protrusion 519 can be formed on the surface 512A of the inner flange portion 51 so as to bend the end portion 615 of the outer flange portion 519.

Other configurations, effects and advantages in the gas sensor according to the present embodiment, are the similar to that of the present embodiment. Likewise, in the present embodiment, elements having the same reference symbols as that of the first embodiment are equivalent to those of the first embodiment.

(Confirmation Test 1)

According to the confirmation test, the air tightness between the insulator 3 and the housing 4 of the gas sensor 1 (test sample) of the first embodiment is confirmed. Specifically, it is confirmed whether an amount of leakage produced between the insulator 3 and the housing 4 is within a required allowable range of leakage limit. Also, a gas sensor is used as a comparative sample, in which the position in the radial direction R of the end face 511 of the inner flange portion 51, and the position in the radial direction R of the end face 611 of the outer flange portion 61 are flush with each other. Then, the air tightness is confirmed for the comparative sample.

In the confirmation test, pressure of the exhaust gas in the pipe is set to be higher than the atmospheric pressure of the reference gas A, in which a pressure difference therebetween is set to be 40 kPa. The inner flange portion 51 and the outer flange portion 61 are heated such that the temperature thereof becomes 600° C. Then, cold-heat cycle is performed for more than 100 times so as to cool the inner flange portion 51 and the outer flange portion 61 such that the temperature thereof becomes 25° C. as the room temperature, thereby heating and cooling the gas sensors of the test sample and the comparative sample. While repeating the cold-heat cycle, mass flow meter measures an amount of flow of the exhaust gas that flows between the insulator 3 and the housing 4, and total accumulated amount of the gas flow is calculated as an amount of leakage.

Figure 24:
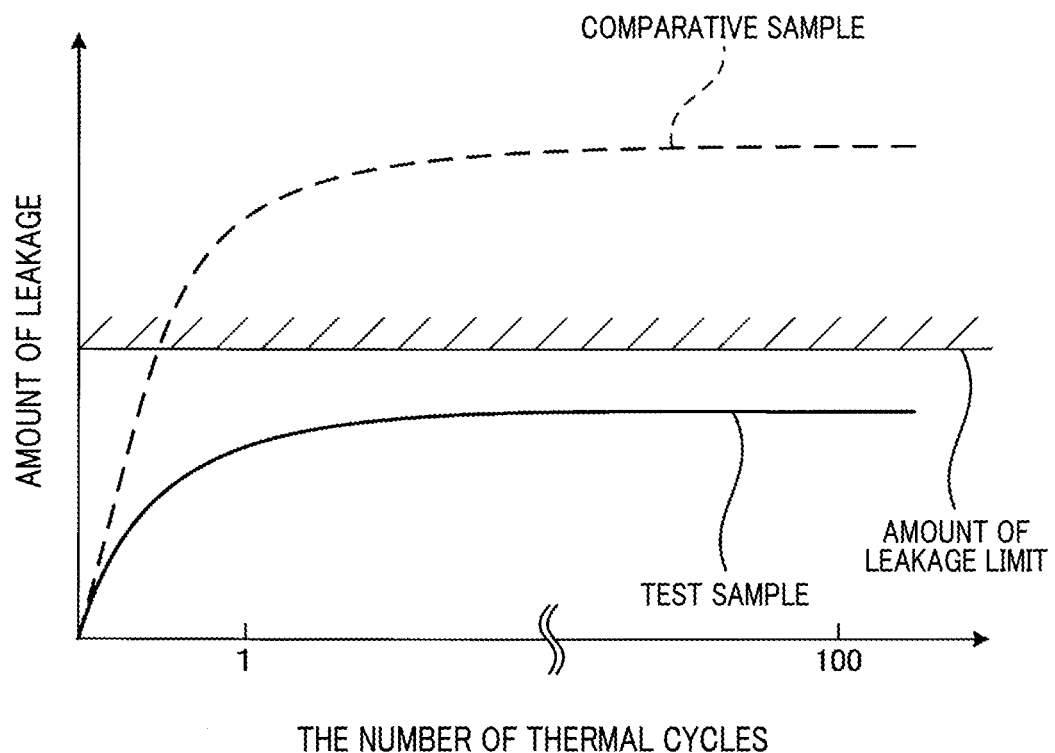
FIG. 24 is a graph showing a leakage variation in repeated thermal cycles for a test sample and a reference sample, during a confirmation test 1.

FIG. 24 illustrates a change in an amount of leakage during the cold-heat cycle. As shown in FIG. 24, the amount of leakages of both the test sample and the comparative sample significantly increase in the first cold-heat cycle and saturate as the cold-heat cycle is repeatedly performed. According to this confirmation test, a required output accuracy of the gas sensor to detect the gas is determined, and an amount of leakage required for secure the output accuracy is determined as an allowable range of leakage limit.

As a result of the confirmation test, the leakage amount of the test sample is lower than the leakage limit. Hence, it was found that the test sample satisfies the required output accuracy for detecting gas. Meanwhile, an amount of leakage of the comparative sample is higher than the leakage limit so that required detection accuracy cannot be satisfied depending on the comparative samples.

(Confirmation Test 2)

According to the confirmation test 2, amount of leakages are confirmed for the test samples 1 to 6 of the gas sensor 1 described in the first and second embodiments, and the comparative samples 1, 2 described in the confirmation test 1, under various conditions of the insulator opposing surface 321, the housing opposing surface 414, the inner flange portion 51 and the outer flange portion 61.

The conditions include relationships between an inclination angle $\alpha$ of the insulator opposing surface 321, an inclination angle $\beta$ of the housing opposing surface 414, and the inclination angle $\gamma$ of the inner flange portion 51 and the outer flange portion 61, such as $\alpha<\gamma\leq\beta$, and $\alpha=\beta=\gamma$. Further, the conditions include a case where the end face 511 of the entire periphery of the inner flange portion 51 in the circumferential direction C is positioned in the outer side R1 of the radial direction R than the end face 611 of the entire periphery of the outer flange portion 61 in the circumferential direction C (expressed as $\Delta L=+$, refer to FIG. 3), and a case where the end face 611 of the entire periphery of the outer flange portion 61 in the circumferential direction C is positioned in the outer side R1 of the radial direction R than the end face 511 of the entire periphery of the inner flange portion 51 in the circumferential direction C (expressed as $\Delta L=-$, refer to FIG. 13). Note that $\Delta L$ refers to a distance between the end face 511 of the inner flange portion 51 and the end face 611 of the outer flange portion 61.

Further, the condition includes a case where the end face 511 of a half periphery of the inner flange portion 51 in the circumferential direction C is positioned in the outer side R1 of the radial direction R than the end face 611 of the half periphery of outer flange portion 61 in the circumferential direction C, and the end face 511 of the remaining periphery is positioned in an inner side of the radial direction R than the end face 611 of the remaining half periphery ($\Delta L=\pm$, refer to FIG. 10); and a case where the position of the end face 611 of the entire periphery of the outer flange portion 61 in the circumferential direction C and the position of the end face 511 of the entire periphery of the inner flange portion 51 in the circumferential direction C are the same ($\Delta L=0$).

The table 1 shows conditions of the confirmation test for the test samples 1 to 6 and the comparative samples 1 and 2, in which a condition of the inclination angle is $\alpha<\gamma\leq\beta$ or $\alpha=\beta=\gamma$, and a positional relationship between the end face 511 of the inner flange portion 51 and the end face 611 of the outer flange portion 61 is $\Delta L=+$, $\Delta L=-$, $\Delta L=\pm$ or $\Delta L=0$. Also, the table 1 includes evaluation result of the leakage amount for the test samples 1 to 6 and the comparative samples 1 and 2, which is evaluated in the same manner as the first confirmation test 1.

TABLE 1

|  | Conditions | Evaluation of leakage amount |
| --- | --- | --- |
| test sample 1 | $\alpha < \gamma \leq \beta$, $\Delta L = +$ | A (excellent) |
| test sample 2 | $\alpha < \gamma \leq \beta$, $\Delta L = -$ | A (excellent) |
| test sample 3 | $\alpha = \beta = \gamma$, $\Delta L = +$ | B (good) |
| test sample 4 | $\alpha = \beta = \gamma$, $\Delta L = -$ | B (good) |
| test sample 5 | $\alpha < \gamma \leq \beta$, $\Delta L = \pm$ | B (good) |
| test sample 6 | $\alpha = \beta = \gamma$, $\Delta L = \pm$ | B (good) |
| comparative sample 1 | $\alpha < \gamma \leq \beta$, $\Delta L = 0$ | C (poor) |
| comparative sample 2 | $\alpha = \beta = \gamma$, $\Delta L = 0$ | C (poor) |

As shown in the table 1, in the case of the test samples 1 and 2 having a relationship of $\alpha<\gamma\leq\beta$, and a relationship $\Delta L=+$ or $\Delta L=-$, the evaluation result was "A (excellent)" since the leakage amount becomes extremely low. Therefore, required output accuracy to detect gas can be sufficiently maintained. On the other hand, in the case of the test samples 3 and 4 having a relationship $\alpha=\beta=\gamma$ and a relationship either $\Delta L=+$ or $\Delta L=-$, the evaluation result was "B (good)" in which the leakage amount is lower than the leakage limit. However, the required output accuracy to detect gas can be still maintained.

Further, in the case of the test samples 5 and 6 having a relationship $\alpha<\gamma\leq\beta$ or $\alpha=\beta=\gamma$, and $\Delta L=\pm$, the evaluation result was "B (good)" in which the leakage amount is lower than the leakage limit. On the other hand, as for the comparative samples 1 and 2 having a relationship $\alpha<\gamma\leq\beta$ or $\alpha=\beta=\gamma$, and a relationship $\Delta L=0$, the evaluation result was "C (poor)" in which the leakage amount exceeds the leakage limit. Hence, it was found that the required output accuracy to detect gas cannot be maintained.

According to the result of the confirmation test, it has been found that the air tightness can effectively maintained because of arrangement of the end face 511 of the inner flange portion 51, and the end face 611 of the outer flange portion 61 in which both positions of the end faces 511 and 611 are mutually offset in the radial direction R. Also, in addition to the offset between the positions of the end face 511 and the end face 611, since the relationship of $\alpha<\gamma\leq\beta$ is satisfied, whereby the air tightness is most effectively maintained.

The present disclosure is not limited to the above-described embodiments. However, various modifications can be made without departing the spirit and scope thereof.

What is claimed is:

1. A gas sensor comprising:

a sensor element having a detecting portion exposed to detection gas to perform gas detection;

an insulator made of a ceramic material, supporting the sensor element in a state where the detecting portion is protruded therefrom, the sensor element being inserted through the insulator;

a housing made of metal disposed in an outer periphery of the insulator, supporting the insulator;

an inner cover made of metal, covering the detecting portion and having an inner through hole that allows the detection gas to flow therethrough; and an outer cover made of metal, covering the inner cover such that a gas passage through which the detection gas flows is formed between the outer cover and the inner cover and having an outer through hole that allows the detection gas to flow therethrough, wherein an inner flange portion formed over an entire periphery of an end portion of the inner cover and an outer flange portion formed over an entire periphery of an end portion of the outer cover are supported between the insulator and the housing;

an end face of the inner flange portion and an end face of the outer flange portion are mutually offset;

a corner portion is formed between the end face and a surface in either one of the inner flange portion and the outer flange portion; and the corner portion formed in either one of the inner flange portion and the outer flange portion protrudes into the surface of the other flange portion, or an end portion in either one of the inner flange portion and the outer flange portion is bent to overhang the corner portion in the other flange portion formed between the end face and the surface.

2. The gas sensor according to claim 1, wherein the end face of the inner flange portion is positioned radially closer to an outer side with respect to a radial direction than a position of the end face of the outer flange portion, where an insertion direction is defined as a direction along which the sensor element is inserted into the insulator, and the radial direction is defined as a direction orthogonal to the insertion direction, extending from a center axis line that passes a center of the sensor element along the insertion direction; and the corner portion of the outer flange portion protrudes into the surface of the inner flange portion, or the end portion of the inner flange portion is bent to overhang the corner portion of the outer flange portion.

3. The gas sensor according to claim 1, wherein the end face of the outer flange portion is positioned radially towards an outer side with respect to a radial direction than a position of the end face of the inner flange portion, where an insertion direction is defined as a direction along which the sensor element is inserted to the insulator, and the radial direction is defined as a direction orthogonal to the insertion direction, extending from a center axis line that passes a center of the sensor element along the insertion direction; and the corner portion of the inner flange portion protrudes into the surface of the outer flange portion, or the end portion of the outer flange portion is bent to overhang the corner portion of the inner flange portion.

4. The gas sensor according to claim 2, wherein a tip end side is defined as a side in the insertion direction, where the detecting portion is protruded from the sensor element, and a rear end side is defined as a side opposite to the tip end side in the insertion direction;

the inner flange portion and the outer flange portion are each formed to be inclined such that positions of the inner flange portion and the outer flange portion with respect to the insertion direction become closer to the rear end side, as positions of the inner flange portion and the outer flange portion with respect to the radial direction become closer to the outer side;

an insulator opposing surface that faces the inner flange portion is formed on an entire outer periphery of the insulator;

a housing opposing surface that faces the outer flange portion is formed on an entire inner periphery, and a relationship $\alpha<\gamma\leq\beta$ or $\alpha\leq\beta<\gamma$ is satisfied, where an inclination angle of the insulation opposing surface with respect to a virtual reference line parallel to the radial direction is defined as $\alpha$, an inclination angle of the housing opposing surface with respect to the virtual reference line is $\beta$ and an inclination angle of the inner flange portion and the outer flange portion with respect to the virtual reference line is $\gamma$.

5. The gas sensor according to claim 3, wherein a tip end side is defined as a side in the insertion direction, where the detecting portion is protruded from the sensor element, and a rear end portion is defined as a side opposite to the tip end side;

the inner flange portion and the outer flange portion are each formed to be inclined such that positions of the inner flange portion and the outer flange portion with respect to the insertion direction become closer to the rear end side, as positions of the inner flange portion and the outer flange portion with respect to the radial direction become closer to the outer side;

an insulator opposing surface that faces the inner flange portion is formed on an entire outer periphery of the insulator;

a housing opposing surface that faces the outer flange portion is formed on an entire inner periphery, and a relationship $\alpha<\beta<\gamma$ is satisfied, where an inclination angle of the insulation opposing surface with respect to a virtual reference line parallel to the radial direction is defined as $\alpha$, an inclination angle of the housing opposing surface with respect to the virtual reference line is $\beta$ and an inclination angle of the inner flange portion and the outer flange portion with respect to the virtual reference line is $\gamma$.

6. A gas sensor comprising:

a sensor element having a detecting portion exposed to detection gas to perform gas detection;

an insulator made of a ceramic material, supporting the sensor element in a state where the detecting portion is protruded therefrom, the sensor element being inserted through the insulator;

a housing made of metal disposed in an outer periphery of the insulator, supporting the insulator;

an inner cover made of metal, covering the detecting portion and having an inner through hole that allows the detection gas to flow therethrough; and an outer cover made of metal, covering the inner cover such that a gas passage through which the detection gas flows is formed between the outer cover and the inner cover and having an outer through hole that allows the detection gas to flow therethrough, wherein an inner flange portion formed over an entire periphery of an end portion of the inner cover and an outer flange portion formed over an entire periphery of an end portion of the outer cover are supported between the insulator and the housing;

a protrusion is formed on a surface in either one of the inner flange portion and the outer flange portion; and the protrusion formed in either one of the inner flange portion and the outer flange portion protrudes into the surface of the other flange portion, or an end portion in either one of the inner flange portion and the outer flange portion is bent to overhang the protrusion formed on the surface in the other flange portion.

* * * * *